United States Patent
Giftakis et al.

(10) Patent No.: US 11,925,806 B2
(45) Date of Patent: Mar. 12, 2024

(54) BRAIN STIMULATION THERAPY

(71) Applicant: Medtronic, Inc., Minneapolis, MN (US)

(72) Inventors: Jonathon E. Giftakis, Maple Grove, MN (US); Paul H. Stypulkowski, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 238 days.

(21) Appl. No.: 16/941,085

(22) Filed: Jul. 28, 2020

(65) Prior Publication Data
US 2020/0353262 A1 Nov. 12, 2020

Related U.S. Application Data

(60) Continuation of application No. 16/036,439, filed on Jul. 16, 2018, now Pat. No. 10,729,908, which is a division of application No. 14/920,468, filed on Oct. 22, 2015, now Pat. No. 10,052,485.

(51) Int. Cl.
*A61N 1/36* (2006.01)
*A61N 1/05* (2006.01)

(52) U.S. Cl.
CPC ....... *A61N 1/36139* (2013.01); *A61N 1/0534* (2013.01); *A61N 1/36082* (2013.01); *A61N 1/36096* (2013.01); *A61N 1/36171* (2013.01)

(58) Field of Classification Search
CPC ............ A61N 1/36139; A61N 1/36082; A61N 1/36096; A61N 1/0534
See application file for complete search history.

(56) References Cited

U.S. PATENT DOCUMENTS

| | | | |
|---|---|---|---|
| 7,668,601 B2 | 2/2010 | Hegland et al. | |
| 8,706,237 B2 | 4/2014 | Giftakis et al. | |
| 10,052,485 B2 | 8/2018 | Giftakis et al. | |
| 10,183,168 B2 | 1/2019 | Baru et al. | |
| 2011/0137371 A1 | 6/2011 | Giftakis et al. | |
| 2012/0271375 A1* | 10/2012 | Wu | A61N 1/36153 607/45 |

(Continued)

OTHER PUBLICATIONS

Stanslaski, et al., "Design and Validation of a Fully Implantable, Chronic, Closed-loop Neuromodulation Device with Concurrent Sensing and Stimulation," Neural Systems and Rehabiliation Engineering, IEEE Transactions, vol. 20, Issue 4, Jan. 23, 2012, 12 pp.

(Continued)

*Primary Examiner* — Rex R Holmes
(74) *Attorney, Agent, or Firm* — Shumaker & Sieffert, P.A.

(57) ABSTRACT

Deep Brain Stimulation (DBS) electrodes are positioned within (or adjacent to) white matter fiber tracts in a brain of patient. The DBS electrodes may be positioned near one or more stimulation sites within the white matter fiber tracts. The stimulation sites may be selected based on the disorder of the patient. In some examples, the stimulation sites may be selected based on one or more symptoms of the patient. In some examples, additional electrodes may be positioned in another area to collect bioelectrical brain signals. The area in which the additional electrodes are placed is an area that is different from the stimulation site but is targeted by stimulation therapy provided at the stimulation site.

16 Claims, 15 Drawing Sheets

(56) References Cited

U.S. PATENT DOCUMENTS

2014/0243926 A1    8/2014   Carcieri
2015/0360033 A1   12/2015   Koubeissi et al.
2018/0326217 A1   11/2018   Giftakis et al.

OTHER PUBLICATIONS

Prosecution History from U.S. Appl. No. 14/920,468, dated from Apr. 19, 2017 through May 15, 2018, 54 pp.
Prosecution History from U.S. Appl. No. 16/036,439, dated from Dec. 26, 2019 through Apr. 7, 2020, 39 pp.

\* cited by examiner

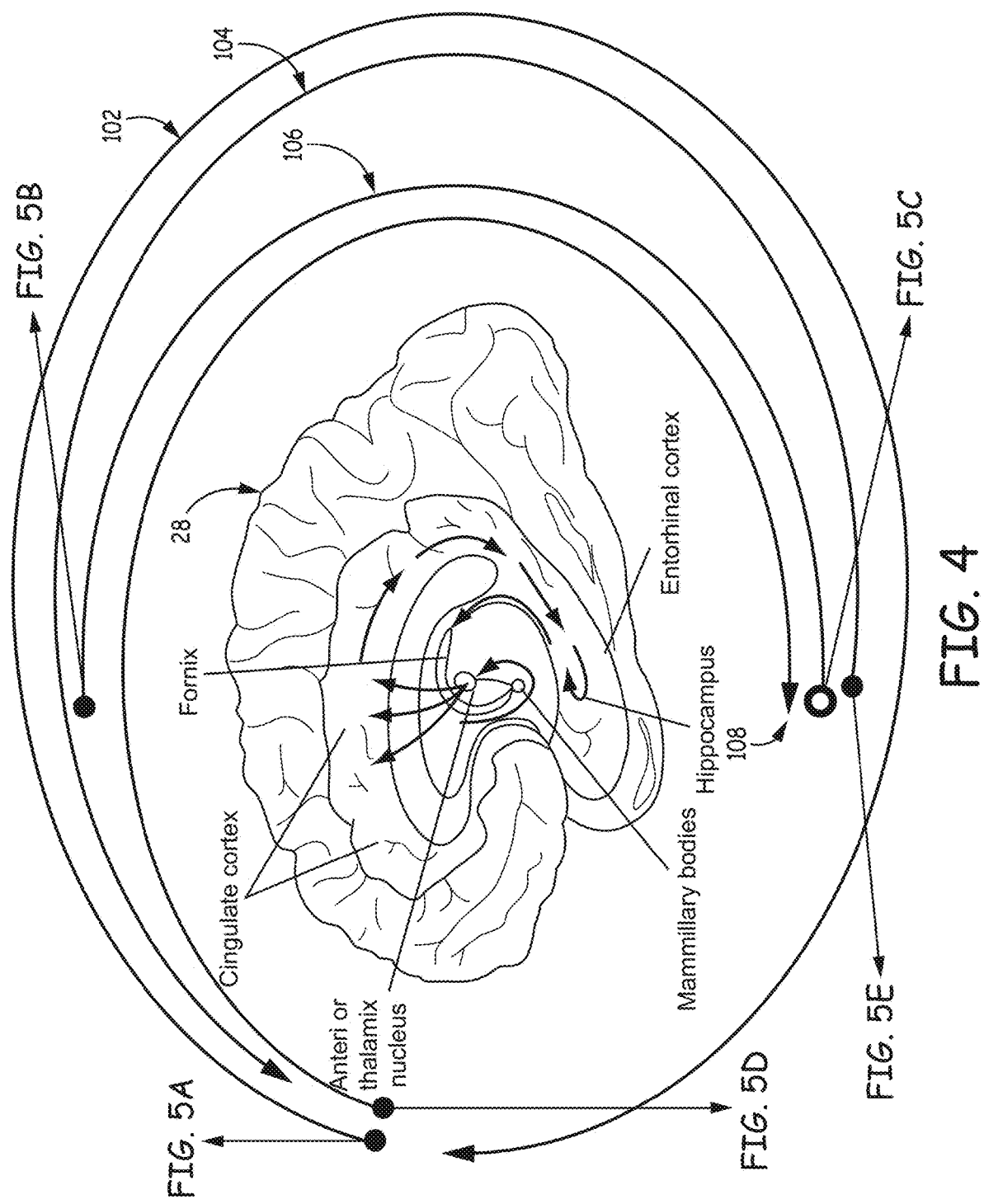

BRAIN STIMULATION THERAPY

CROSS-REFERENCE TO RELATED APPLICATIONS

This application is a continuation of U.S. patent application Ser. No. 16/036,439, filed on Jul. 16, 2018 (now U.S. Pat. No. 10,729,908, issued Aug. 4, 2020), which is a divisional of U.S. patent application Ser. No. 14/920,468, filed on Oct. 22, 2015 (now U.S. Pat. No. 10,052,485, issued Aug. 21, 2018). The entire content of each of applications Ser. No. 16/036,439 and 14/920,468 are incorporated herein by reference.

TECHNICAL FIELD

The disclosure relates to brain stimulation therapy.

BACKGROUND

Implantable medical devices, such as electrical stimulators may be used in different therapeutic applications, such as deep brain stimulation (DBS) or. A medical device may be used to deliver therapy to a patient to treat a variety of symptoms or patient conditions such as chronic pain, tremor, Alzheimer's disease, Parkinson's disease, other types of movement disorders, seizure disorders (e.g., epilepsy), obesity or mood disorders. In some therapy systems, an external or implantable electrical stimulator delivers electrical therapy to a tissue site within a patient with the aid of one or more implanted electrodes, which may be deployed by medical leads or on a housing of the stimulator.

SUMMARY

In general, the disclosure is direct to methods and systems for delivering electrical stimulation to a brain of a patient.

In one example, the disclosure is directed to a method for delivering electrical stimulation, the method comprising: providing, via at least one electrode implanted in a brain of a patient, electrical stimulation at a low frequency to a stimulation site within a white matter tract of the patient, the electrical stimulation having an intensity; detecting at least one peak in an evoked potential signal received in response to electrical stimulation; and providing, via the at least one electrode, therapeutic electrical stimulation at the intensity and a relatively higher frequency.

In another example, the disclosure is directed to a method comprising: delivering, via at least one electrode implanted in a patient's brain, electrical stimulation at a specific stimulation frequency to the patient's brain; sensing bioelectrical brain activity comprising a bioelectrical response to the delivery of the electrical stimulation; detecting a biomarker in the bioelectrical response, the biomarker occurring during the delivery of the electrical stimulation, the biomarker comprising oscillation in the bioelectrical response at a frequency that is one of a sub-harmonic frequency of the specific stimulation frequency or a physiologically driven frequency different from the specific stimulation frequency; and adjusting at least one parameter of the electrical stimulation based on the detected biomarker.

In another example, the disclosure directed to a system comprising: at least one electrode configured to be implanted in a brain of a patient; an electrical stimulation generator configured to provide, via the at least one electrode, stimulation at a low frequency to a stimulation site within a white matter tract of the patient, the electrical stimulation having an intensity; and a sensing module configured to detect a bioelectrical brain signal from the patient; a processor configured to detect at least one peak in the bioelectrical brain signal received in response to the electrical stimulation; and wherein the electrical stimulation generator is further configured to provide, via the at least one electrode, therapeutic electrical stimulation at the intensity and a relatively higher frequency.

In another example, the disclosure is directed to a system comprising: an electrical stimulation generator configured to deliver, via at least one electrode implanted in a brain of a patient, electrical stimulation at a specific frequency to the brain; a sensing module configured to sense bioelectrical brain activity comprising a bioelectrical response to the delivery of electrical stimulation; and a processor configured to detect a biomarker in the bioelectrical response, the biomarker occurring during the delivery of electrical stimulation, the biomarker comprising oscillation in the bioelectrical response, and wherein the frequency of oscillation is one of a sub-harmonic frequency of the specific stimulation frequency, or physiologically driven frequency different from the specific stimulation frequency, and adjust at least one electrical stimulation therapy parameter based on the detected biomarker.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 4 is a conceptual diagram illustrating example regions of a brain of a patient, including the Circuit of Papez.

DETAILED DESCRIPTION

Figure 1:
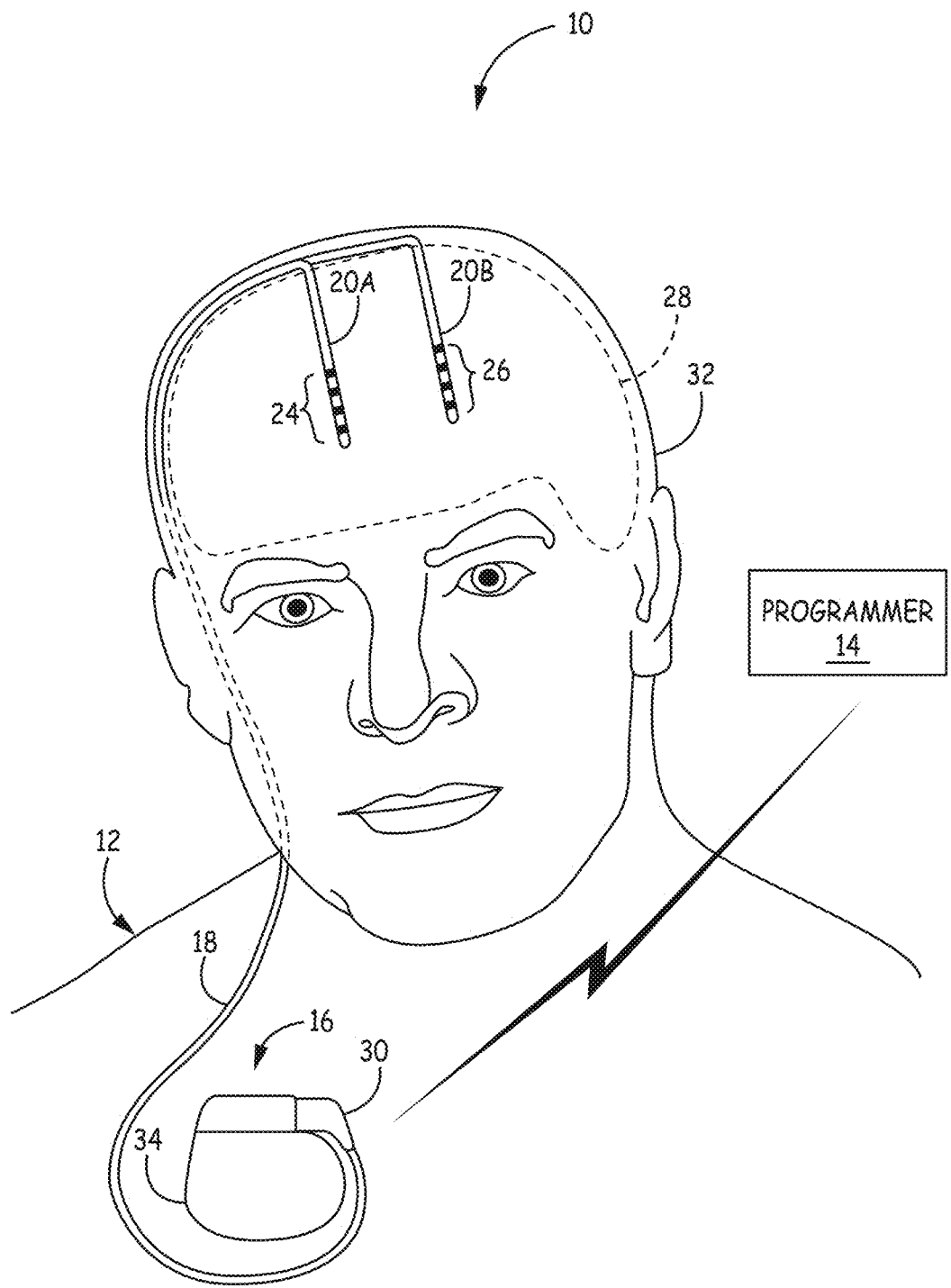
FIG. 1 is a conceptual diagram illustrating an example therapy system that is configured to delivery therapy to a patient.

In some examples consistent with the present disclosure, DBS stimulation is used to manage one or more symptoms of a patient disorder. In some examples, DBS electrodes are positioned within (or adjacent to) white matter fiber tracts in a brain of patient. The DBS electrodes may be positioned near one or more stimulation sites within the white matter fiber tracts. The stimulation sites may be selected based on the disorder of the patient. In some examples, the stimulation sites may be selected based on one or more symptoms of the patient. In some examples, additional electrodes may be positioned in another area to collect bioelectrical brain signals. In some examples, the area in which the additional electrodes are placed is an area that is different from the stimulation site but is targeted by stimulation therapy provided at the stimulation site. For example, additional sensing electrodes may be placed in the hippocampus (HC), whereas stimulation electrodes may be placed in a different area, such as the anterior nucleus (AN). In some examples, the additional electrodes may be external to the patient and may sense a scalp EEG.

In some examples, DBS electrodes are positioned in, or adjacent to, white matter fiber tracts which have been identified for stimulation for a specific patient. The target location for the DBS electrodes may be determined during preoperative MRI imaging assessment, or with diffusion tensor imaging (DTI), for example. In some examples, additional electrodes are positioned in a targeted area for brain sensing, which is different from, but connected to, the stimulation site. The targeted area for brain sensing may be connected to the stimulation site through white matter projections.

In some examples, during implantation, evoked potentials in a bioelectrical signal measured in response to stimulation delivered from different combinations of electrodes, e.g., different electrode pairs may be used to determine neural connectivity with a target site. Based on the evoked potentials, a set of electrode pairs may be selected to provide therapeutic electrical stimulation. In some examples, electrical stimulation is provided to the white matter fiber tract at a relatively low frequency. For example, stimulation is provided at a relatively low frequency less than approximately 15 Hertz (Hz). In some examples, the relatively low frequency is between approximately 2 Hz and 10 Hz. In some examples, stimulation is provided at a relatively low frequency of approximately 5 Hz. In some examples, the stimulation is provided iteratively at ascending amplitudes, while maintaining a relatively low frequency. Stimulation amplitude may a voltage amplitude stimulation parameter or a current amplitude stimulation parameter.

The evoked potential is measured in response to each application of stimulation. In some examples, the stimulation intensity is increased by increasing the voltage amplitude stimulation parameter. In some examples, the stimulation intensity is increased by increasing the current amplitude stimulation parameter. The stimulation intensity may be increased at predetermined intervals. In some examples, the voltage may be increased from approximately 1.5 V to approximately 7 V in a series of individual 0.5 V intervals. Based on the evoked potentials detected, an electrode pair may be selected for delivery of therapeutic stimulation. In some examples, the evoked potentials associated with the selected electrode pair may include a single peak in response to a low intensity level of applied stimulation and two discrete peaks in response to a relatively higher intensity level of applied stimulation. In some examples peaks in the sensed signal may be detected by comparing the sensed signal to one or more thresholds. In examples where multiple electrode pairs result in evoked potentials with a desired response, such as a single peak in response to a low intensity level of stimulation and/or two discrete peaks at a relatively higher intensity level of stimulation, an electrode pair may be selected based on the difference in stimulation intensities required to elicit the single peak and the two discrete peaks. For example, the electrode pair with the greatest difference between the two intensities of stimulation may be selected. In other examples, the electrode pair with the lowest stimulation intensity needed to achieve a single peak in the evoked potential may be selected.

In some examples, one or more stimulation parameter values for therapeutic stimulation may be selected based on characteristics of the evoked potentials sensed during the programming stage. For example, the electrode pair for providing the stimulation may be selected based on which electrode pair, of a plurality of different electrode pairs, results in the desired evoked potential at a target site. In some examples, the stimulation intensity selected for the therapeutic stimulation delivered via the selected electrode pair may also be based on the evoked potentials. For example, stimulation may be provided at the level of stimulation intensity to result in a single peak in order to inhibit local field potential (LFP) activity at the target site. The level of simulation intensity may indicate the appropriate voltage amplitude, stimulation amplitude, or both, for therapeutic stimulation providing an inhibitory effect, e.g., reducing or inhibiting LFP activity at the target site. In some examples, the stimulation therapy is provided at a higher frequency than the stimulation which resulted in peaks detected during programming. For example, inhibitory therapy may be provided at a frequency between approximately 30 Hz and 150 Hz. In some examples, inhibitory therapy may be provided with stimulation at a frequency of approximately 40 Hz. The inhibitory effect is short acting and lasts approximately as long as stimulation is provided. Inhibitory stimulation therapy may be applied in order to mitigate symptoms resulting from an excess of activity at the target site. For example, inhibitory stimulation therapy may be used to lower the likelihood of a seizure in epilepsy patients.

In another example, one or more stimulation parameters may be selected in order to provide an excitatory effect at the target site. For example, therapeutic stimulation may be provided to the stimulation site in order to excite the target site, which may be at or remote from the stimulation site. The stimulation parameters for excitatory stimulation are different than those which result in an inhibitory response. In some examples, the stimulation frequency and electrode combination may be approximately the same for both excitatory and inhibitory stimulation. For example, the stimulation may be provided at a frequency between approximately 30 Hz and 150 Hz. Although the electrode combination and frequency stimulation parameters may be the same for both inhibitory and excitatory therapy, the stimulation intensity is different. The difference in stimulation intensity may be the result of a difference in voltage amplitude or current amplitude. The stimulation intensity for excitatory stimulation therapy may be determined based on analysis of the evoked potentials from the target site. In some examples, the stimulation intensity for excitatory stimulation therapy is approximately equal to the stimulation intensity which resulted in an evoked potential with two discrete peaks. Stimulation provided at a frequency of approximately 50 Hz and a stimulation intensity which resulted in two discrete peaks in the evoked potential during programming may have an excitatory effect on the target site during the application of the stimulation. In some examples, the excitatory effect stops at approximately the same time the application of stimulation stops. Excitatory therapy may be used to, for example, facilitate memory recall, improve cognitive function or improve patient mood. In some examples, the response to the excitatory therapy may be called a chirp. A chirp may include a short acting inhibition to the target site followed by an excitatory response which lasts until approximately the end of the application of stimulation.

While in the foregoing example, stimulation intensity is different for inhibitory versus excitatory stimulation, in other examples, the stimulation intensity may be the same for excitatory stimulation versus inhibitory stimulation. In this alternative example, one or more of the electrode combination and frequency of stimulation may be different between the two types of stimulation.

The timing of stimulation induces chirp cycling, e.g., repeated chirps, to provide excitatory drive to a neural circuit may vary depending on the application. In some examples, the timing of therapy cycles may be optimized to maintain a desired brain state. The stimulation may be provided at predetermined intervals, or in response to a change in patient brain state, for example. In examples where a change in brain state is detected, stimulation may be applied in order to induce chirps until the patient brain state has reverted to the previous, desired, state. In some examples, chirp inducing stimulation may be provided in response to a patient input. For example, a patient may self-administer stimulation therapy, via control of a stimulator with a patient programmer, in response to an undesired cognitive or mode change. The patient may self-administer the stimulation therapy via control of a stimulator with a patient programmer, for example.

In some examples, stimulation is provided to a specific stimulation frequency at a stimulation site. The stimulation may induce changes in a sensed bioelectrical brain signal including oscillation within the sensed bioelectrical brain signal. The oscillation in the sensed bioelectrical brain signal is at a frequency other than that of the applied stimulation. In some examples, the oscillation frequency in the sensed bioelectrical brain signal may be at a sub-harmonic of the specific stimulation frequency. In other examples, the oscillation frequency of the sensed bioelectrical brain signal may be a physiological driven frequency. For example, the simulation may excite a portion of the brain to generate a native signal which is at a different frequency than the stimulation, and is not a harmonic or sub-harmonic of the stimulation frequency. In some examples, the oscillation in the sensed bioelectrical brain signal may last for the duration of the application of stimulation. In other examples, the oscillation in the sensed bioelectrical brain signal may be self terminating, and may terminate before stimulation is terminated. In some examples, the induced oscillation may provide a therapeutic effect if the time of oscillation is above a first predetermined threshold, but below a second predetermined threshold. The first predetermined threshold may be the threshold time of oscillation before an effect is detected. The second predetermined threshold may be the time at which negative effects from the oscillation is detected.

FIG. 1 is a conceptual diagram illustrating an example therapy system 10 that is configured to deliver therapy to patient 12 to manage a disorder of patient 12. In some examples, therapy system 10 may deliver therapy to patient 12 to manage symptoms of a neurological disease (e.g., Alzheimer's disease) of patient 12. Therapy system 10 may be used to manage the symptoms of patient 12 by facilitating memory recall, improving cognitive functioning, improving motor functioning, improving mood, minimizing seizures, or minimizing tremors, for example. The symptoms controlled by therapy system 10 may be dependent upon the diagnosis of Patient 12, as well as the relative severity of symptoms. Patient 12 ordinarily will be a human patient. In some cases, however, therapy system 10 may be applied to other mammalian or non-mammalian non-human patients. While examples of the disclosure are described in some cases with regard to management of symptoms of Alzheimer's disease, in other examples, therapy system 10 may also provide therapy to manage symptoms of patient conditions, such as, but not limited to, Alzheimer's disease, seizure disorders such as epilepsy, Parkinson's disease, psychological disorders, mood disorders, movement disorders or other neurogenerative impairment.

Therapy system 10 includes medical device programmer 14, implantable medical device (IMD) 16, lead extension 18, and one or more leads 20A and 20B (collectively "leads 20) with respective sets of electrodes 24, 26. IMD 16 includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28). In some examples, stimulation is delivered to the white matter tract of brain 28 to determined neural connectivity between a stimulation site and a target site in another region of brain 28. For example, during programming, stimulation may be provided via a plurality of different electrode pairs or a combination of more than two electrodes, and the electrode combination providing the most efficacious response may be determined based on evoked potentials. In some examples, therapeutic stimulation may be used to either provide intermittent excitatory drive to a neural circuit, or to inhibit said circuit, based on the stimulation parameters Electrical stimulation generated from the stimulation generator (shown in FIG. 3) of IMD 16 may help prevent the onset of events associated with the patient's disorder or mitigate symptoms of the disorder. For example, electrical stimulation therapy delivered by IMD 16 to a stimulation site within brain 28 may facilitate memory recall, improve cognitive function, or improve mood, thereby relieving one or more symptoms of Alzheimer's disease by exciting or inhibiting a target site.

IMD 16 may deliver electrical stimulation therapy to brain 28 of patient 12 according to one or more stimulation therapy programs. A therapy program defines one or more electrical stimulation parameter values for therapy generated and delivered from IMD 16 to brain 28 of patient 12. In examples in which IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy program may include one or more electrode combinations, which can include selected electrodes (e.g., selected from electrodes 24, 26) and their respective polarities. The exact therapy parameter values of the stimulation therapy that helps prevent or mitigate symptoms, such as the amplitude or magnitude (electrical current or voltage) of the stimulation signals, the duration of each signal (e.g., in the case of stimulation pulses, a pulse width or duty cycle), the waveform of the stimuli (e.g., rectangular, sinusoidal or ramped signals), the frequency of the signals, cycling (whether stimulation is always on, or whether it is cycled on and off for predetermined periods of time) and the like, may be specific for the particular stimulation site (e.g., the area of the brain) involved as well as the particular patient and patient condition. While stimulation pulses are primarily described herein, stimulation signals may be of any form, such as continuous-time signals (e.g., sine waves) or the like.

In addition to delivering stimulation therapy to manage a symptom of patient 12, therapy system 10 is configured to monitor one or more bioelectrical brain signals of patient 12. For example, IMD 16 may include a sensing module that senses bioelectrical brain signals within one or more regions of brain 28. In some examples, the sensing module of IMD 16 may receive the bioelectrical signals from electrodes 24, 26 or other electrodes positioned to monitored brain signals of patient 12. In the example shown in FIG. 1, the signals generated by electrodes 24, 26 are conducted to the sensing module within IMD 16 via conductors within the respective lead 20A, 20B. Electrodes 24, 26 may also be used to deliver electrical stimulation from the therapy module to stimulation sites within brain 28 as well as sense brain signals within brain 28. In some examples, the sensing module of IMD 16 may sense bioelectrical brain signals via one or more of the electrodes 24, 26 that are also used to deliver electrical stimulation to brain 28. In some examples, the sensed bioelectrical brain signals may be collected near the target site. In other examples, one or more of electrodes 24, 26 may be dedicated to sensing bioelectrical brain signals while one or more different electrodes 24, 26 may be dedicated to delivering electrical stimulation. In some examples, the stimulation site for stimulation and the sensing site may be different. The sensing site may be the same or different from the target site.

As described in further detail below, in some examples, bioelectrical signals sensed by IMD 16 within brain 28 of patient 12 or a separate sensing device implanted or external to patient 12 may be used to select a stimulation site. The stimulation site is the location within brain 28 at which IMD 16 delivers electrical stimulation in order to achieve the desired effect at the target site. In some cases, one or more electrodes 24, 26 are implanted at the stimulation site. In this way, the implantation site for electrodes 24, 26 of leads 20 or the electrode combination (e.g., the subset of electrodes 24, 26) with which IMD delivers electrical stimulation to brain 28 can be selected based on the stimulation site for patient 12. In some examples, the stimulation site may be different than the target site. The target site is the portion of the brain intended to be modulated by the delivery of therapy.

Depending on the particular stimulation electrodes and sense electrodes used by IMD 16, IMD 16 may monitor brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a bioelectrical brain signal of patient 12 may be monitored with external electrodes, e.g., scalp electrodes positioned over a temporal lobe of brain 28. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the examples primarily referred to herein for ease of description, the sensing module and therapy module of IMD 16 are enclosed within a common outer housing 34.

Bioelectrical brain signals monitored and sensed by IMD 16 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LFP) sensed from within one or more regions of a patient's brain and/or action potentials from single cells within brain 28.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 is constructed of a biocompatible material that resists corrosion and degradation from bodily fluids. IMD 16 can comprise a hermetic outer housing 34, which substantially encloses components, such as a processor, therapy module, and memory.

In the example shown in FIG. 1, leads 20 are implanted within the right and left hemispheres, respectively, of brain 28 in order deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere or IMD 16 may be coupled to a single lead that is implanted in one or both hemispheres of brain 28.

Leads 20 may be positioned to deliver electrical stimulation to one or more target tissue sites within brain 28 to manage patient symptoms associated with a condition of patient 12. Leads 20 may be implanted to position electrodes 24, 26 at a target implantation site within brain 28 via any suitable technique, such as through respective burr holes in a skull of patient 12 or through a common burr hole in the cranium 32. Leads 20 may be placed at any location within brain 28 such that electrodes 24, 26 are capable of providing electrical stimulation to one or more stimulation sites within brain 28 during treatment.

Different neurological or psychiatric disorders may be associated with activity in one or more of regions of brain 28, which may differ between patients. For example, in the case of a seizure disorder or Alzheimer's disease, leads 20 may be implanted to deliver electrical stimulation to regions within the Circuit of Papez, such as, e.g., the anterior nucleus (AN), the internal capsule, the cingulate, the fornix, the mammillary bodies, the mammillothalamic tract (mammillothalamic fasciculus), and/or hippocampus (HC). Regions of brain 28 may be functionally connected to one another via neurological pathways such that activity or stimulation provided within one region of brain 28 may affect activity within another region of brain 28. For example, electrical stimulation delivered by IMD 16 to a particular region of brain 28 may influence brain signals in one or more other regions of brain 28. In some examples, brain activity can be indicated by a signal characteristic (e.g., an amplitude, frequency, and/or frequency domain characteristic) of a bioelectrical brain signal. As an example, the signal characteristic of a bioelectrical brain signal sensed within a particular region of brain 28 may change as the brain activity in the region changes.

One example of functionally connected regions of brain 28 includes the Circuit of Papez (described below with respect to FIG. 4). Electrical stimulation delivered from IMD 16 to a particular region of the Circuit of Papez may influence brain signals in one or more other regions of the Circuit of Papez.

As described in further detail below, in some examples, stimulation is provided at a relatively low frequency to the white matter tract (fornix) of brain 28 to determine neural connectivity to another portion of brain 28. In other examples, stimulation may be provided to the white matter tract of brain 28 in order to either inhibit or excite a target area of the brain. In some examples, stimulation may be provided in one portion of the Circuit of Papez in order to inhibit or excite other portions of the Circuit of Papez. A target implantation site for electrodes 24, 26 of leads 20 or senses activity in brain 28, or both, may be selected based on the pathway within brain 28 desired to activated or inhibited. In some examples, the specific electrodes 24, 26 may be chosen during implantation based on which electrodes actually provide stimulation resulting in the desired control of the target site.

A stimulation site may be selected based on the effect of stimulation delivered to a location within the white matter tract at a relatively low frequency. For example, stimulation may be provided at a frequency between approximately 2 Hz and approximately 10 Hz. The effect of the stimulation provided at the stimulation site on a target site may be monitored. Stimulation may be provided at a low frequency at a range of amplitudes, and bioelectrical signals from a target site in the brain may be monitored for evoked potentials. In some examples the signal may be a LFP signal. In some examples electrogortigorgraph (EcoG) or electroencephalogram (EEG) signals are monitored for evoked potentials. A stimulation site and/or electrode pair for providing stimulation may be selected based on which electrodes or what location results in the detection of desired evoked potentials from the target site. Accordingly, the stimulation site may be selected based on the effect of low frequency electrical stimulation delivered to a first region of brain 28 on the brain activity in a second region of brain 28 that is different than the first region, but functionally connected to the first region.

A target implantation site for electrodes 24, 26 of leads 20, an electrode combination with which IMD 16 delivers stimulation to brain 28 or senses activity in brain 28, or both, may be selected based on the stimulation site. In some examples, a temporary lead may be placed to determine appropriate implantation and stimulation sites. In some examples, a target implantation site may be selected based on the symptom being treated. In some examples described herein, a target implantation site for electrodes 24, 26 of leads 20 is selected based on brain activity within one region of the Circuit of Papez while a low frequency electrical stimulation signal is delivered to a different region of the Circuit of Papez. As an example, a stimulation site within an AN of brain 28 can be selected based on the extent of a functional connection between the stimulation site and a HC of brain 28. The relative strength of a functional connection between the AN and the HC may be characterized by the effect of stimulation delivery to a region of the AN on the brain activity level within the HC. In some examples described herein, a meaningful functional connection between an area of the AN and the HC is identified when, as the amplitude of stimulation increases, two peaks appear within the sensed evoked potential sensed from the HC. In other examples, stimulation may be applied to the fornix, for example, and evoked potentials may be monitored in the HC. Again, a meaningful connection may be indicated when, as stimulation amplitude increases, two discrete peaks appear within the sensed bioelectrical brain signal from the target site of the HC. While examples in which a stimulation site within the Fornix of brain 28 is selected based on brain activity within the HC are primarily referred to herein, in other examples, the techniques described herein may also be used to select a stimulation site within regions of brain 28 other than the fornix, or based on connections with a region of the brain other than the HC.

In some examples, stimulation at low frequencies (e.g. between approximately 2 and 10 Hz) is delivered to a stimulation site within the white matter tract to determine neural connectivity to a target site. The connection between the two regions of brain 28 is characterized by the effect of stimulation at a low frequency to a first region of brain 28 on a brain activity level within the second region of brain 28. In some cases, a level of brain activity in a region of brain 28 is indicated by one or more characteristics of a bioelectrical brain signal sensed within the second region of brain 28 or within a different region of brain 28 known to have a functional connection to the second region. The level of brain activity within brain 28 can be indicated by, for example, an amplitude of a bioelectrical brain signal, a variance of the bioelectrical brain signal over time, or a frequency domain characteristic (e.g., an energy level within one or more specific frequency bands) of the bioelectrical brain signal. The amplitude value may comprise an average, peak, median or instantaneous amplitude value over a period of time or a maximum amplitude or an amplitude in a particular percentile of the maximum (e.g., an amplitude value that represents 95% of the maximum amplitude value). In addition, in some examples, the amplitude value may be an absolute amplitude value or a root mean square amplitude value.

IMD 16 may deliver therapy to the brain 28 in a manner that influences the brain signals within one or more regions of brain 28. For example, IMD 16 may deliver therapy to the fornix, or other suitable region of brain 28 to control a brain state of patient 12 (e.g., as indicated by bioelectrical brain signals sensed within the Circuit of Papez) in a manner that effectively treats a disorder or symptom of patient 12. For example, in the case of a Alzheimer's disease, IMD 16 may deliver therapy to a region of brain 28 via a selected subset of electrodes 24, 26 (referred to herein as an electrode combination) to either suppress or excite a level of brain activity within another region of the brain. For example, stimulation may be provided to the fornix to either inhibit or excite activity in another region of the brain implicated in Alzheimer's disease.

IMD 16 may deliver therapy to brain 28 via a selected subset of electrodes 24, 26 to change one or more characteristics of a bioelectrical brain signal exhibited in one or more regions of brain 28 that is associated with an undesirable baseline brain state (e.g., a baseline brain state exhibited by patient 12 in the absence of therapy) to characteristics associated with a desirable brain state. In a desirable brain state, the bioelectrical brain signals sensed via the sensing module of IMD 16 may be indicative of a patient state in which the patient condition is treated, e.g., one or more of symptoms of the patient disorder are mitigated or even eliminated. For example, in the case of a seizure disorder, in a desirable brain state, the possibility of an onset of a seizure or a severity, duration, or frequency of seizures may be reduced. In other examples, the desired brain state may include an increase in activity in a region. For example, activation of a region may enable better cognitive function of the patient, or aid in memory recall tasks or elevate a patient mood.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields. The complex electrode array geometry may include multiple electrodes (e.g., partial ring or segmented electrodes) around the perimeter of each lead 20, rather than a ring electrode. In some examples, electrodes 24, 26 may include one or more full ring electrodes in combination with one or more segmented electrodes. An example would be a "1-3-3-1" lead having a distal ring electrode; two rows each having three segmented electrodes, and a more proximal ring electrode. Such a lead is described in U.S. Pat. No. 7,668,601 assigned to the assignee of the current application. In still other examples, the complex electrode array may comprise electrodes formed using thin film techniques and the array may comprise any number of electrodes, such as forty or more electrodes. In this manner, electrical stimulation may be directed to a specific direction from leads 20 to enhance therapy efficacy and reduce possible adverse side effects from stimulating a large volume of tissue. In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, one or both leads 20 may have a shape other than elongated cylinders as shown in FIG. 1. For example, leads 20 may be paddle leads, spherical leads, bendable leads, or any other type of shape effective in treating patient 12.

External programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, e.g., a power button, or the buttons and the keypad may be soft keys that change in function depending upon the section of the user interface currently viewed by the user. In some examples, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, information on patient anatomy (e.g., imaging data such as CT or MRI data) and any other information that may be useful for programming into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may provide efficacious therapy to patient 12 to address symptoms associated with the seizure disorder (or other patient condition). During the programming session, patient 12 may provide feedback to the clinician as to the efficacy of the specific program being evaluated or the clinician may evaluate the efficacy based on one or more physiological parameters of patient (e.g., heart rate, respiratory rate or muscle activity).

Programmer 14 may also assist the clinician in the identification of a target implantation site for leads 20 or an electrode combination for stimulation therapy delivery for patient 12. For example, as discussed with respect to FIGS. 6-8, programmer 14 can display indications of a plurality of areas within the white matter tract of brain 28 (which may each be an potential stimulation site) and one or more associated metrics, where the metrics indicate the measured relative functional connection between the respective area of the white matter tract and a target site of brain 28. Based on the displayed metrics, a clinician may select one or more of the areas of the white matter tract as a stimulation site. In some examples, programmer 14 may associate each of the areas of the white matter tract with a particular subset of electrodes 24, 26, such that programmer 14 or the clinician may also select an electrode combination for therapy delivery based on the displayed bioelectrical brain signals.

Programmer 14 may also be configured for use by patient 12 in some examples. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Whether programmer 14 is configured for clinician or patient use, programmer 14 is configured to communicate to IMD 16 and, optionally, another computing device, via wireless communication. Programmer 14, for example, may be configured to communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may provide stimulation on a periodic basis, or on demand. In some examples, programmer 14 may be patient programmer whereby a patient may initiate the delivery of stimulation. For example, patient 12 may provide input initiating excitatory stimulation in order to improve cognitive function, memory, or mood. In other examples, patient 12 may provide input indicating the effect desired, and programmer 14 will select between a plurality of programs based on the desired effect. The desired effect may be, for example, either excitatory or inhibitory stimulation. In some examples, stimulation may be provided in response to detecting a predetermined biomarker within a sensed bioelectrical brain signal. In some examples, the sensed bioelectrical brain signal may be an LFP. In some examples, stimulation may be provided at predetermined times of the day. The predetermined times of day may align with certain behaviors of patient 12. For example, waking or sleeping.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment. In addition, the trial stimulator can be used to select a target therapy delivery site for patient 12.

Figure 2:
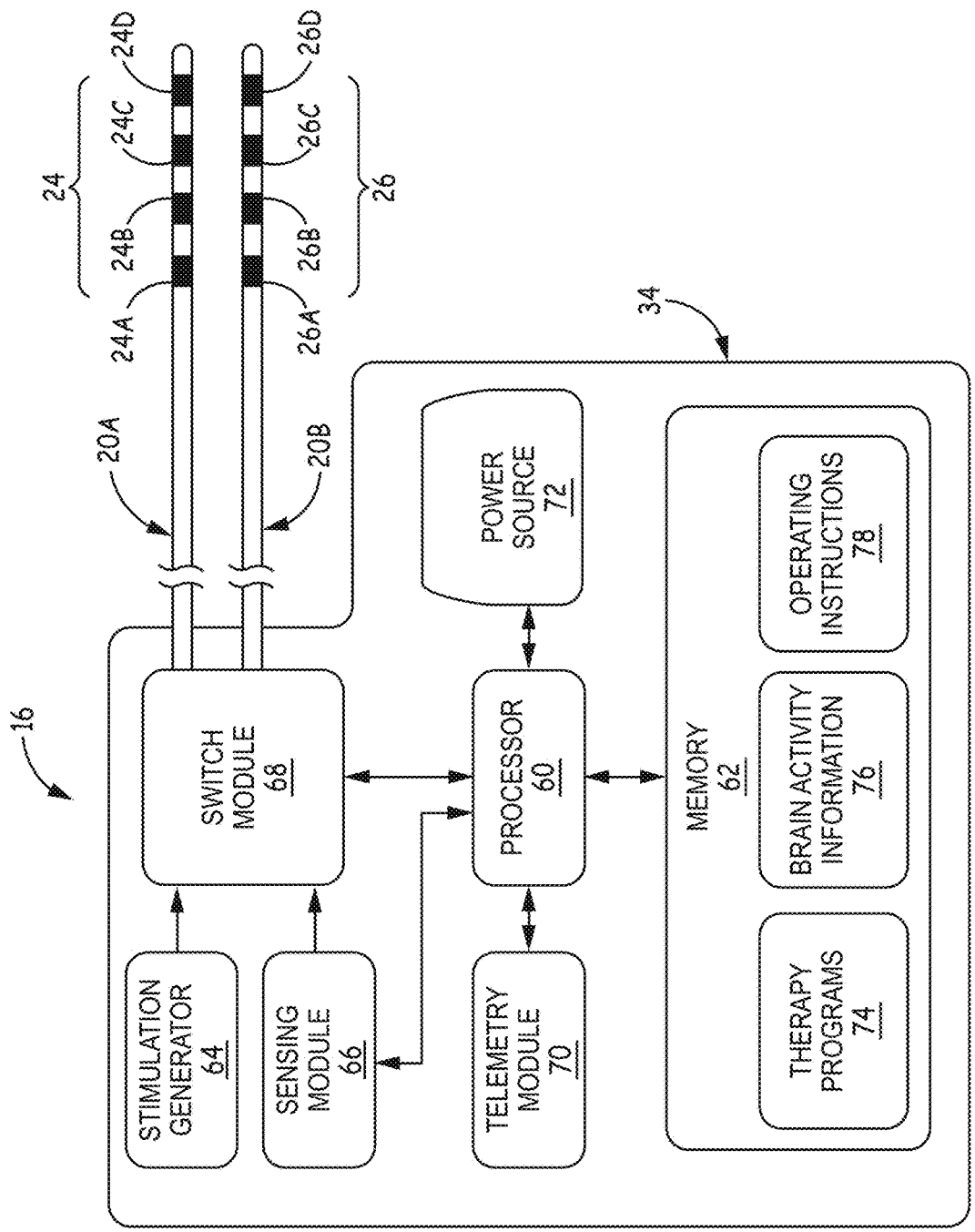
FIG. 2 is a functional block diagram illustrating components of the implantable medical device in FIG. 1.

FIG. 2 is functional block diagram illustrating components of IMD 16. In the example shown in FIG. 2, IMD 16 includes processor 60, memory 62, stimulation generator 64, sensing module 66, switch module 68, telemetry module 70, and power source 72. Memory 62 may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74, brain activity information 76, and operating instructions 78 in separate memories within memory 62 or separate areas within memory 62. Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal. In examples when IMD 16 delivers electrical stimulation therapy on a cyclic basis (as compared to on demand), memory 62 stores, e.g., as part of therapy programs 74, cycle parameter information, such as, on cycle time duration and off cycle duration. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Brain activity information 76 stored by memory 62 can include information collected during the mapping of the functional connection between plurality of areas of the Fornix of brain 28 and the HC of brain 28 (e.g., using the techniques described with respect to FIGS. 6 and 7), as well as any other information indicative of activity within one or more regions of brain 28. Examples of information stored by brain activity information 76 include, but are not limited to, bioelectrical brain signal data generated by sensing module 66 via at least one of electrodes 24, 26 and, in some cases, at least a portion of outer housing 34 of IMD 16, an electrode on outer housing 34 of IMD 16 or another reference, and biomarkers indicative of a functional connection between a particular area of the fornix of brain 28 and the HC of brain 28.

In some examples, processor 60 may determine the brain activity level within a particular region of brain 28 of patient 12 based on bioelectrical brain signals sensed by sensing module 66 via a subset of electrodes 24, 26, which may be referred to herein as a sense electrode combination. Thus, in some examples, processor 60 stores sensed bioelectrical brain signals as brain activity information 76. Operating instructions 78 guide general operation of IMD 16 under control of processor 60, and may include instructions for monitoring brains signals within one or more brain regions via electrodes 24, 26 and/or selecting one or more therapy cycle parameters based on the monitored brain signals. Operating instructions 78 may also include instructions for selecting one or my therapy parameters based on input from a user.

Stimulation generator 64, under the control of processor 60, generates stimulation signals for delivery to patient 12 via selected combinations of electrodes 24, 26. In some examples, during therapy delivery (versus mapping neural connections) to manage a patient symptom, stimulation generator 64 generates and delivers stimulation signals to one or more target regions of brain 28 (FIG. 1), e.g., the fornix, of patient 12 via a selected combination of electrodes 24, 26 (referred to herein as a stimulation electrode combination) where the stimulation signals have a frequency in a range of about 30 Hertz (Hz) to about 150 Hz, a voltage of about 0.1 volts to about 10.5 volts, and a pulse width of about 60 microseconds to about 450 microseconds. In some examples, the stimulation signals have a frequency of 40 Hz, a voltage of about 3 volts, and a pulse width of about 150 microseconds. In addition, in some examples, the stimulation signals have a frequency of 40 Hz, a voltage of about 6 volts, and a pulse width of about 150 microseconds.

In some examples, stimulation frequency may be maintained while voltage amplitude is varied to either inhibit or excite the HC of brain 28. For example, stimulation at approximately 40 Hz and 2 volts may inhibit activity along the GABAERGIC pathway, while stimulation at approximately 40 Hz and 6 volts may have excitatory effects on the antidromic and cholinergic pathways.

During the selection of a stimulation site within the fornix of brain 28, processor 60 controls stimulation generator 64 to generate and deliver relatively low frequency stimulation, such as stimulation signals having a between approximately 2 and 10 Hz. In some examples, the stimulation signals have a frequency of approximately 5 Hz. Stimulation is provided at a constant frequency, with the amplitude of the stimulation slowly increasing over time. For example, stimulation may be provided starting at approximately 1.5 V and be incrementally increased to approximately 8 V, e.g., in intervals of 0.5V. Other stimulation parameter values, and other therapy cycles are contemplated. Other ranges of therapy parameter values may also be useful, and may depend on the stimulation site within patient 12, which may or may not be within brain 28.

Processor 60, alone or in combination with sensing module 66, is configured to detect one or more biomarkers in the sensed bioelectrical brain signals. For example, during programming, processor 60 may detect the presence of one or more peaks in the sensed bioelectrical brain signal. In some examples, processor 60 is configured to determine at what stimulation intensity a single peak first appears in the sensed bioelectrical brain signal. This information may be stored in memory 62. Processor 60 is also configured to determine at what stimulation intensity two distinct peaks appear in the sensed bioelectrical brain signal. The stimulation intensity may be stored in memory 62. In some examples, processor 60 is configured to detect oscillation in the sensed bioelectrical brain signal. Processor 60 may determine the length of time the oscillation in the amplitude of the sensed bioelectrical brain signal is present, as well as the frequency of the oscillation.

Processor 60 may include any one or more of a microprocessor, a controller, a digital signal processor (DSP), an application specific integrated circuit (ASIC), a field-programmable gate array (FPGA), discrete logic circuitry, and the functions attributed to processor 60 herein may be embodied as firmware, hardware, software or any combination thereof. Processor 60 is configured to control stimulation generator 64 according to therapy programs 74 stored in memory 62 to apply particular stimulation parameter values specified by one or more programs, such as amplitude, pulse width, and pulse rate.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across the electrodes 24, 26 of the selected stimulation electrode combination.

Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68. For example, in some examples each electrode is connected to a dedicated controllable current source and current sink.

Stimulation generator 64 may be a single channel or multi-channel stimulation generator. In particular, stimulation generator 64 may be capable of delivering, a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66 is configured to sense bioelectrical brain signals of patient 12 via a sense electrode combination, which can include a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). As previously described, processor 60 may monitor the brain state of patient 12 via the sensed bioelectrical brain signals. In examples without a switch module 68, processor 60 may select each electrode individually. In some examples, processor 60 may select an electrode combination for delivering efficacious stimulation therapy to patient 12 based on one or more characteristics of the bioelectrical brain signals monitored by sensing module 66. In addition, in some examples, an implantation site for leads 20 may be selected based on one or more characteristics of the bioelectrical brain signals monitored by sensing module 66. Although sensing module 66 is incorporated into a common outer housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 supports wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information 76 to programmer 14 via telemetry module 70.

Power source 72 is configured to deliver operating power to various components of IMD 16. Power source 72 may include, for example, a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
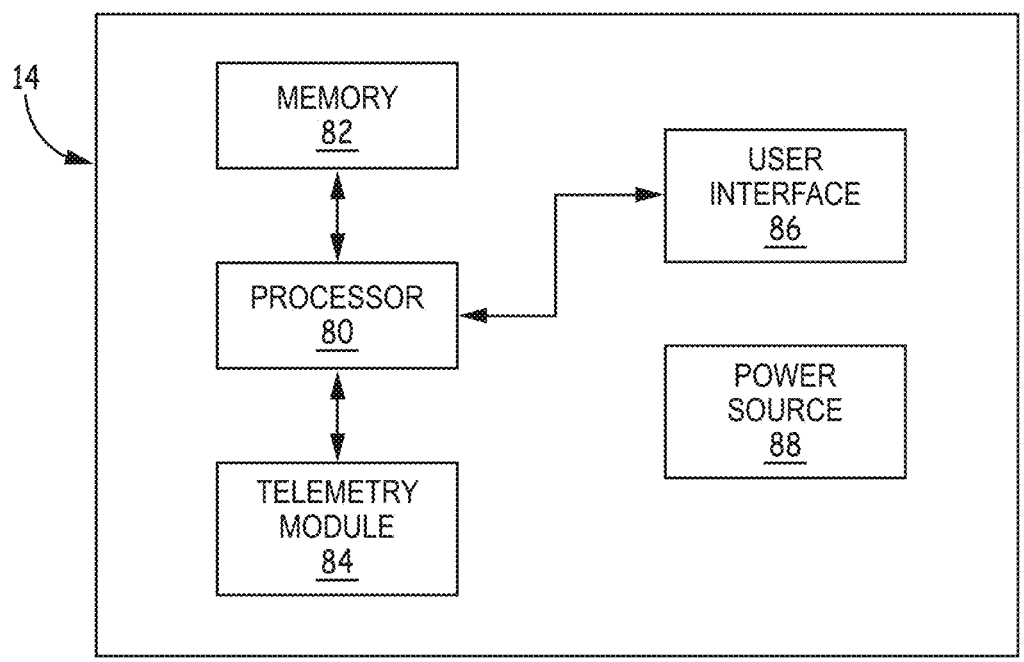
FIG. 3 is a functional block diagram illustrating components of an example medical device programmer.

FIG. 3 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, to present information related to the therapy, such as information related to bioelectrical signals sensed via a plurality of sense electrode combinations in response to the delivery of stimulation to brain 28. In addition, user interface 86 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 80 of programmer 14 and provide input.

As discussed above, if programmer 14 includes buttons and a keypad, the buttons may be dedicated to performing a certain function, or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 86 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, dedicated keys within user interface 86 may be associated with a particular symptom. Patient 12 initiate the delivery of stimulation to alleviate a symptom simply by pressing the key associated with the particular symptom. In some examples, processor 80 may limit the number of times stimulation may be provided within a certain time frame in response to patient input.

In some examples, at least some of the control of stimulation delivery by IMD 16 may be implemented by processor 80 of programmer 14. For example, in some examples, processor 80 may control stimulation generator 64 of IMD 16 to generate and deliver electrical stimulation to a plurality of areas of the fornix of brain 28 and may further control sensing module 66 to sense a bioelectrical brain signal within brain 28 that is indicative of the brain activity level within the HC of brain 28. For example, each of a plurality of symptoms may be associated with a different stimulation site within the fornix. As described in further detail below, in some cases, the bioelectrical brain signal that indicates the brain activity level within the HC may be sensed within the HC or may be sensed within the AN, the fornix, or another region of the brain. Although the Circuit of Papez normally flows from the HC to the fornix, stimulation provided at appropriate levels may override the normal flow of the circuit and cause activity to flow from the fornix to the HC. Processor 80, automatically or with the aid of a clinician, may select one or more of the areas of the fornix as a stimulation site based on the brain activity level within the HC of brain 28 associated with the areas of the fornix. For example, in the case of a Alzheimer's disease, processor 80 may select the one or more areas of the AN associated with mood for a first stimulation site, a second area associated with memory for a second stimulation site, and a third area associated with cognitive function as a third stimulation site.

Memory 82 may include instructions for operating user interface 86 and telemetry module 84, and for managing power source 88. Memory 82 may also store any therapy data retrieved from IMD 16, such as, but not limited to, brain activity information. The clinician may use this therapy data to determine the progression of the patient condition in order to plan future treatment for the disorder (or patient symptoms) of patient 12. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 88 may include circuitry to monitor power remaining within a battery. In this manner, user interface 86 may provide a current battery level indicator or low battery level indicator when the battery needs to be replaced or recharged. In some cases, power source 88 may be capable of estimating the remaining time of operation using the current battery.

FIG. 4 is a conceptual diagram illustrating example regions of brain 28 of patient 12 and, in particular, regions of brain 28 included in the Circuit of Papez (also referred to as the Papez Circuit). The Circuit of Papez is one of the major pathways of the limbic system, and the regions of brain 28 within the Circuit of Papez includes the AN, internal capsule, cingulate (labeled as the cingulate cortex in FIG. 4), HC, fornix, entorhinal cortex, mammillary bodies, and mammillothalamic tract (MMT). The regions of brain 28 within the Circuit of Papez may be considered to be functionally related (also referred to herein as functionally connected), such that activity within one part of the Circuit of Papez may affect activity within another part of the Circuit of Papez. In this way, the delivery of stimulation to one region (e.g., the AN) of the Circuit of Papez may affect the brain activity level within another region of the Circuit of Papez (e.g., the HC).

In some examples, electrodes 24, 26 are implanted to deliver electrical stimulation therapy generated via stimulation generator 64 (FIG. 2) to and/or monitor bioelectrical brain signals within one or more regions of the brain in the Circuit of Papez, such as, e.g., the AN, the internal capsule, the cingulate, the fornix, the mammillary bodies, the mammillothalamic tract, and/or HC. In some examples, a disorder of patient 12 may be effectively managed by controlling or influence the brain activity level within one or more regions of the Circuit of Papez. For example, with respect to seizure disorders, therapy may be delivered from IMD 16 to regions within the Circuit of Papez to suppress brain activity (also referred to as cortical activity) within regions of the Circuit of Papez, such as, e.g., the HC. Suppression of brain activity within the HC via therapy may reduce the likelihood of a seizure by patient 12. As another example, for treatment of Alzheimer's disease, therapy may be delivered from IMD 16 to regions within the Circuit of Papez to increase cortical activity within the regions of the Circuit of Papez, such as, e.g., the HC. Increasing brain activity within the HC via therapy may reduce symptoms of Alzheimer's disease, such as memory loss.

The effect of stimulation at a first location within the Circuit of Papez on a second location (or on the same location) is shown in greater detail with respect to FIGS. 5A-5E discussed below. Pathway 102 illustrates a pathway through the entire Circuit of Papez from AN to AN. The effect of stimulation applied to the AN on the AN along pathway 102 is show in FIG. 5A. Pathway 104 illustrates a path from the HC to the AN. The effect of stimulation applied to the HC on the AN is shown in FIG. 5E. Pathway 106 illustrates a path from HC to the fornix and back from the fornix to the HC. The effect on stimulation applied to the HC on the fornix is shown in FIG. 5B, while the effect of stimulation applied to the fornix on the HC is shown in FIG. 5C. Pathway 108 illustrates a path from the AN to the HC. The effect of stimulation applied to the AN on the HC is shown in FIG. 5D.

Figure 5A:
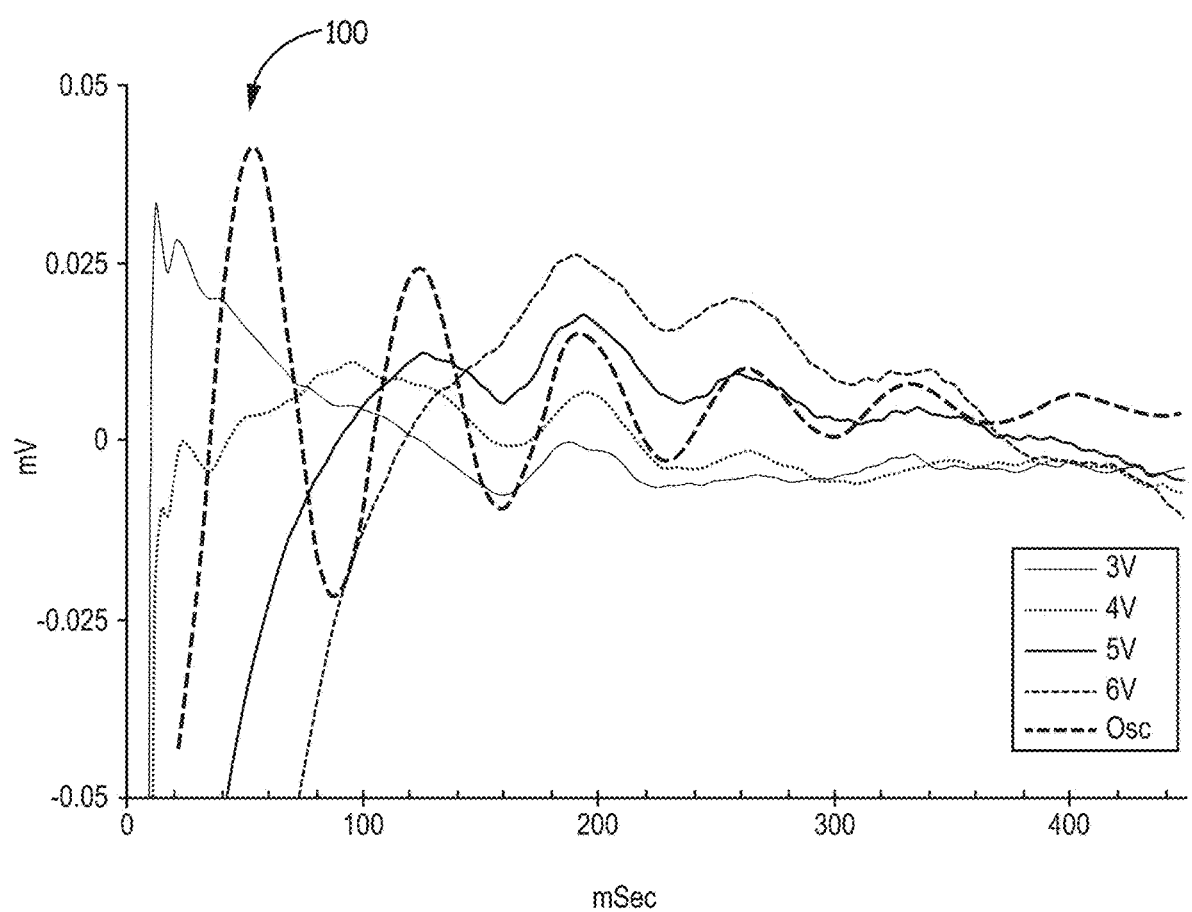
FIGS. 5A-5E are graphical illustrations of evoked potential response to the application of stimulation in various regions of the brain.
Figure 5B:
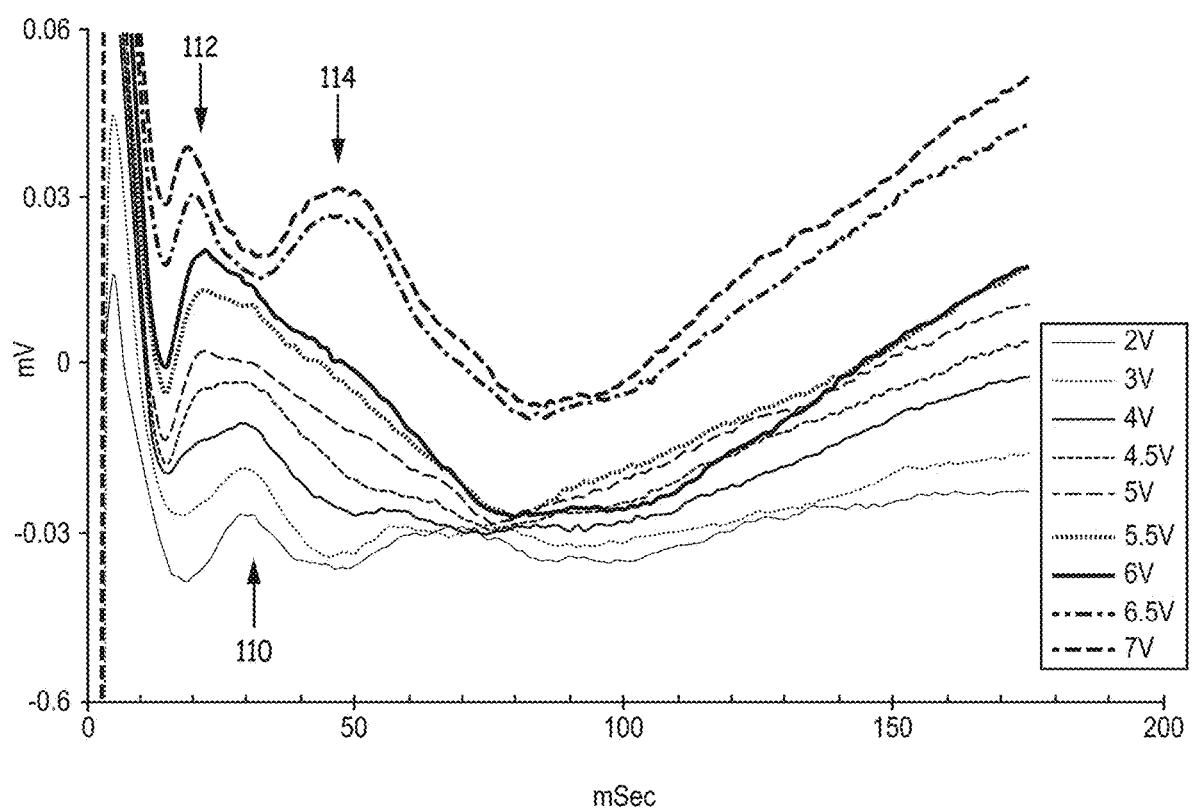
Figure 5C:
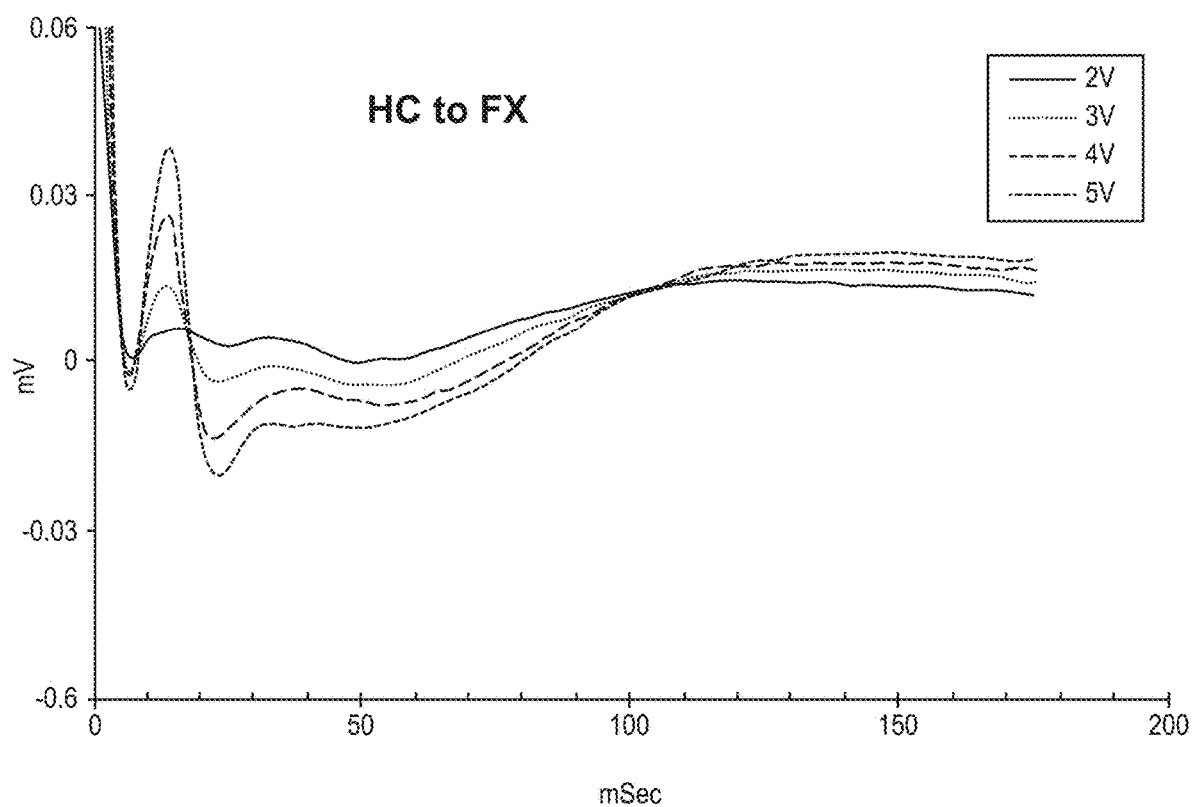
Figure 5D:
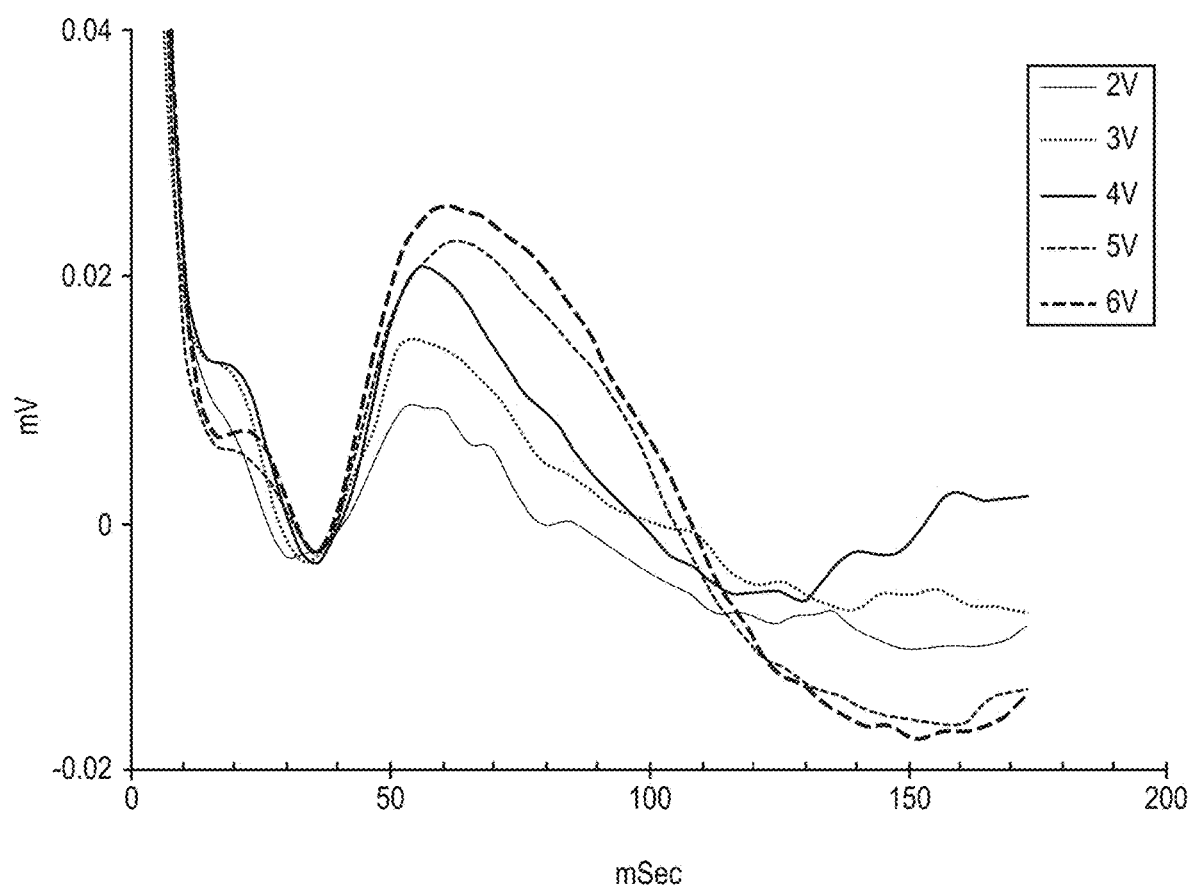
Figure 5E:
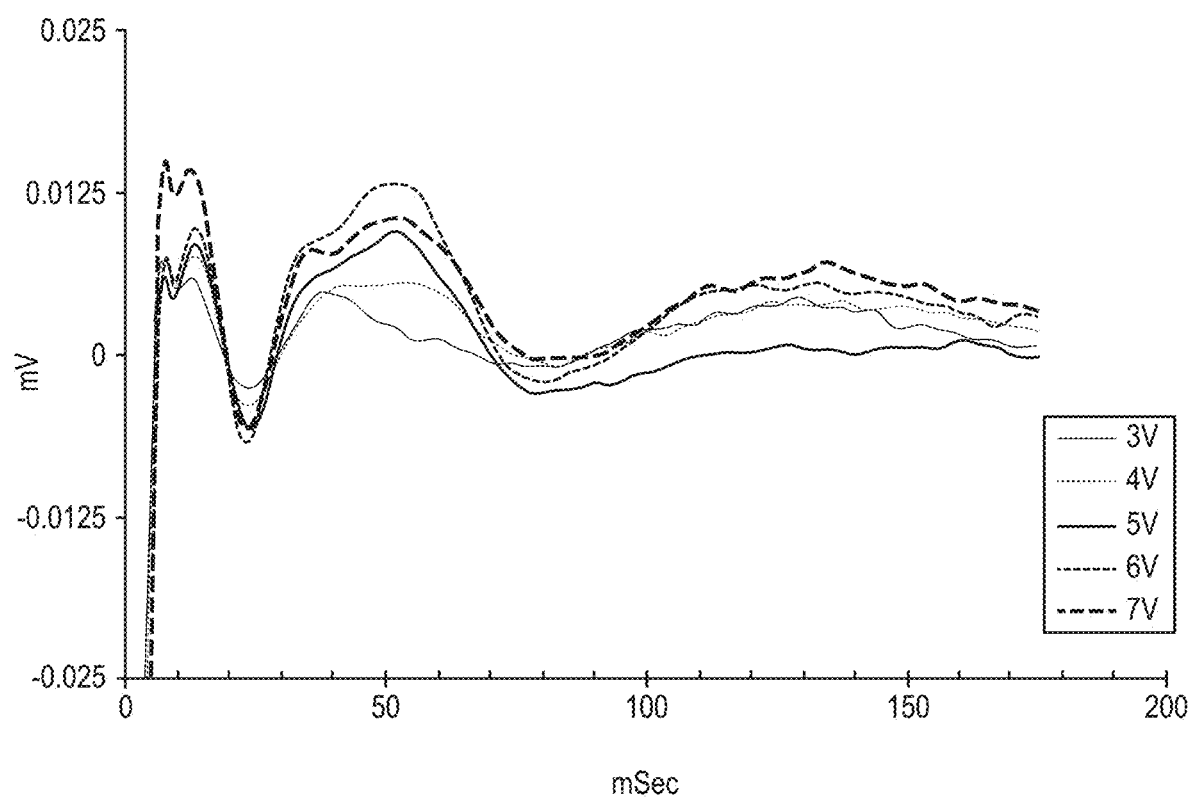

FIG. 5A is a graph illustrating the evoked potential amplitude sensed in the AN in response to stimulation to the AN at various voltages, with a constant frequency. As shown in FIG. 5A, stimulation provided to the AN may induce a response in the AN which oscillates at a frequency different than the frequency of stimulation. The x-axis of FIG. 5A is in milliseconds (msec) and the y-axis is in mV. The y-axis indicates the amplitude of the evoked potential in response to stimulation applied at various voltage amplitudes ranging from 3 V to 6V. As shown in FIG. 5A, trace 100 indicates a sub-harmonic frequency of the applied stimulation. The sensed bioelectrical brain activity in response to the application on stimulation to the AN oscillates at a sub-harmonic of the applied stimulation. In some examples, the induced oscillations may result in improvements to a patient condition.

FIG. 5B is a graph illustrating evoked potential amplitude sensed in the HC in response to stimulation to the fornix at various voltages, with a constant frequency. The x-axis of FIG. 5B is in msec, and the y-axis is in mV. The y-axis indicates the amplitude of the evoked bioelectrical response of HC to stimulation applied to the fornix. As shown in FIG. 5B, stimulation at a voltage of approximately 2 V to approximately 6 V results in a single peak 110 in the evoked potential signal. This peak 110 indicates activation of the GABAERGIC pathway, and inhibition of LFP activity within the HC. As the voltage increases, the location of peak 110 shifts from approximately 30 msec towards approximately 15-20 msec. Eventually, the single peak 110 disappears around approximately 6.5V and instead two distinct peaks 112 and 114 appear in the sensed evoked potential. Peak 112 is at approximately 15-20 msec and peak 114 is at approximately 50 msec or greater. Peak 112 indicates antidromic firing, while the later peak 114 indicates activation of the cholinergic pathway. These activations indicate an excitatory effect on the HC from the application of stimulation in the fornix.

FIG. 5C is a graph illustrating evoked potential amplitude sensed in the Fornix (FX) in response to stimulation in the HC at various voltages, with a constant frequency. The x-axis of FIG. 5C is in msec, and the y-axis is in mV. The y-axis indicates the amplitude of the evoked bioelectrical response of the FX to stimulation applied to the HC. As indicated in FIG. 5C, the evoked potential signal includes a first peak at approximately 15-20 msec that increases with increased amplitude of stimulation. This peak is followed by a dip, and then the evoked potential signal levels off. The graph indicates that stimulation to the Fornix results in activity in the HC.

FIG. 5D is a graph illustrating the evoked potential amplitude sensed in the HC in response to stimulation provided to the AN at various voltages, with a constant frequency. As stimulation voltage increases, the peak in the evoked potential widens and increases in amplitude. The x-axis of FIG. 5D is in milliseconds (msec) and the y-axis is in mV. The y-axis indicates the amplitude of the evoked potential in response to stimulation applied at various voltage amplitudes ranging from 2 V to 6V.

FIG. 5E is a graph illustrating the evoked potential amplitude sensed in the AN in response to stimulation provided to the HC at various voltages. The x-axis of FIG. 5E is in msec and the y-axis is in mV. The y-axis indicates the amplitude of the evoked potential in response to stimulation applied at various voltage amplitudes ranging from 3 V to 7 V. The evoked potential includes two distinct peaks, one at approximately 10-20 msec and another starting at approximately 40 msec.

Figure 6:
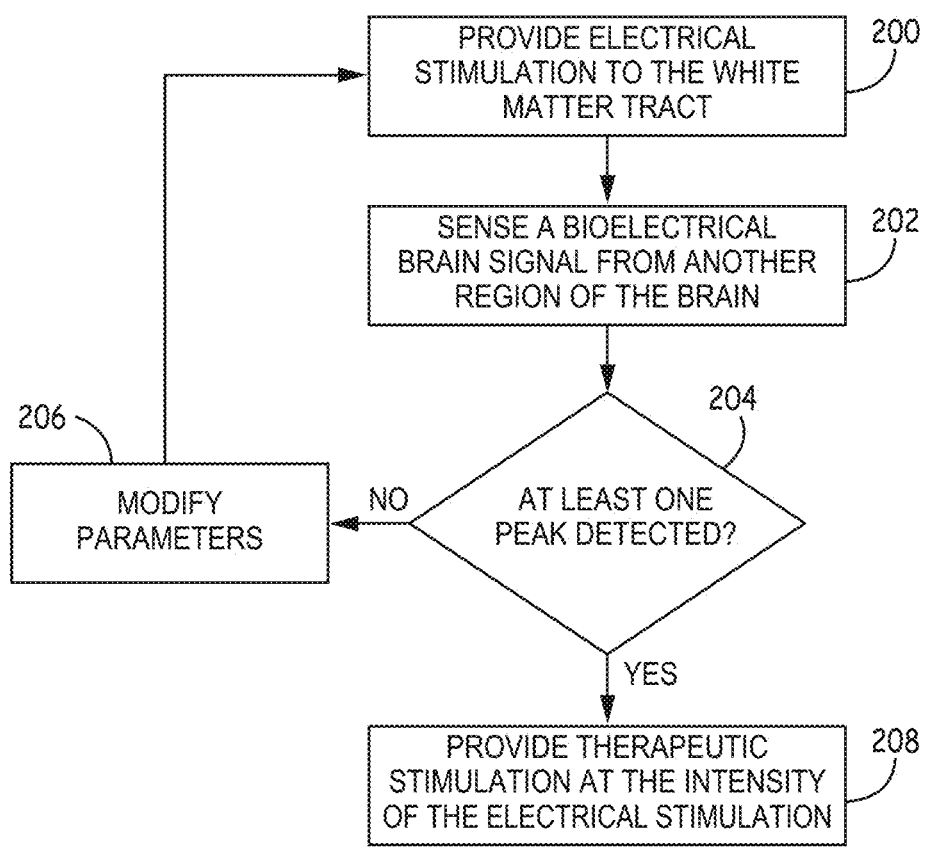
FIG. 6 is a flowchart illustrating an example method consistent with this disclosure.

FIG. 6 is a flowchart illustrating an example technique for determining neural connectivity between the white matter tract of brain 28 and another region of the brain 28, consistent with the present disclosure. Although processing of the detected signals is discussed with respect to IMD 16, all or part of the processing may occur at external programmer 14. Stimulation generator 64 of IMD 16 provides electrical stimulation to the white matter (200) at a first set of therapy parameters. In some examples, the set of stimulation parameters may include a parameter value of a frequency between approximately 2 Hz and 10 Hz. The set of stimulation parameters may also include a combination of electrodes 24, 26, e.g., with one electrode as an anode and one electrode as a cathode in one example. In some examples, the frequency parameter value for the stimulation pulses may be approximately 5 Hz. The stimulation pulse intensity may be initially set at a low level. For example, the stimulation voltage may be approximately 2 V. In other examples, stimulation intensity may be adjusted by a combination of voltage (or current) amplitude, frequency and pulse width.

IMD 16 senses a bioelectrical brain signal from another region of the brain (202). In some examples, the other region of brain 28 may be the HC. IMD 16 may sense the bioelectrical brain signal through the same electrode combination as is used to provide therapy. For example, the electrode combination used to provide therapy may also sense a far field bioelectrical brain signal indicative of the activity in the other region of brain 28.

In other examples, the bioelectrical brain signal may be detected by different electrodes at or near the region of interest. IMD 16 determines if at least one peak is detected (204) within the sensed bioelectrical brain signal that is evoked in response to the stimulation. In some examples, processor 60 determines if at least one peak is present in the sensed bioelectrical brain signal. In other examples, analysis of the sensed brain signal may be done by processor 80 of external programmer 14.

If no peak is detected, then IMD 16 modifies at least one parameter of the stimulation (206), and repeats the process (200, 202, 204). In some examples, modification of at least one parameter may include increasing a stimulation voltage or a stimulation intensity. If the stimulation intensity is below a maximum intensity level, then the intensity of the stimulation is increased. For example, the stimulation voltage may be increased from 2 V to 3V. If the stimulation intensity is at a predetermined maximum intensity level, then IMD 16 changes the electrode pair delivering the stimulation and provides electrical stimulation starting at the baseline stimulation intensity until a peak in the sensed evoked potential is detected.

Once one peak is detected within the sensed bioelectrical brain signal that is evoked in response to the stimulation, IMD 16 is programmed to provide therapeutic stimulation at the intensity of the electrical stimulation (208) which resulted in the peak. In some examples, the therapeutic stimulation provides an inhibitory effect on the target site. In some examples, the therapeutic stimulation provide an excitatory effect on the target site. In some examples, two peaks are detected in the sensed bioelectrical brain signal. When two peaks are detected, providing therapeutic stimulation at the intensity of the electrical stimulation (208) that resulted in the peaks provides excitatory effects on the target site. In some examples, stimulation can be delivered that alternates between providing an excitatory effect and an inhibitory effect on the target site.

In some examples, the process of adjusting stimulation until one or two peaks are detected may be repeated for each possible electrode combination, or a subset of electrode combinations. The therapeutic stimulation may be provided in either a closed-looped or open-looped fashion. For example, the stimulation may be provided in response to detecting a particular brain state, until a desired brain state is achieved. Alternatively, the therapeutic stimulation is provided in response to patient input.

In some examples wherein programmer 14 includes buttons, a keypad, a touch screen, voice activation, or some other user input mechanism, the user may be allowed to indicate a certain type of stimulation that is desirable, such a receiving inhibitory versus excitatory stimulation, via a dedicated user input mechanism. For instance, the user may be allowed to hit a button or other user input feature dedicated to "inhibitory stimulation" or "excitatory stimulation" to select the type of stimulation to start receiving. In other examples, the user may be allowed to provide a voice activated command to start the type of stimulation that is desired. Such options may be useful if the patient has, for instance, a movement disorder that would make it difficult to input more specific parameter changes to cause the stimulation to be delivered. In another example, one or more motion or posture detection sensors such as accelerometers, gyroscopes, etc. may be worn by the patient or carried by clothing to sense patient motion and/or posture. The sensed motion and/or posture signal may be communicated (e.g., wirelessly) to the programmer and/or the IMD to allow the IMD to begin delivering the appropriate stimulation type. For instance, such sensors may be used to detect tremor or a seizure and automatically trigger the delivery of the appropriate type of stimulation to treat the condition.

In some examples, therapeutic stimulation may be provided in a hybrid manner—in response to either a detected state, or patient input. In other examples, stimulation may be provided based on a predetermined schedule.

Figure 7:
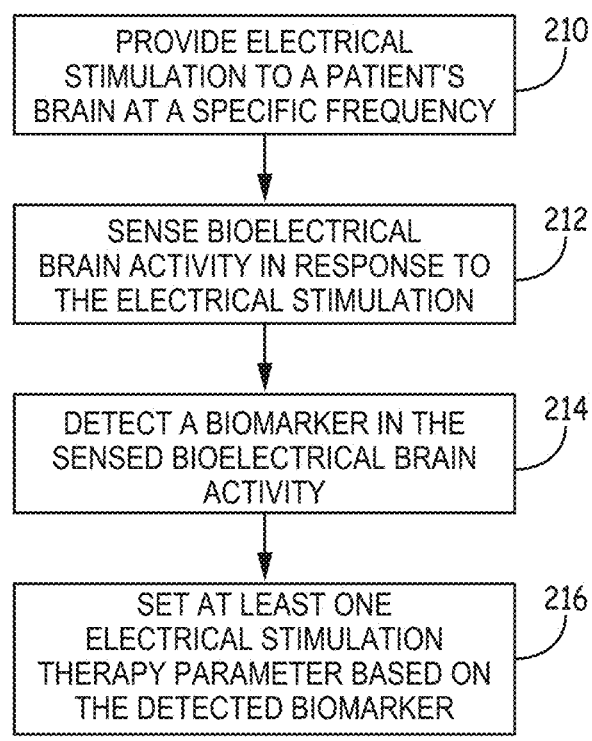
FIG. 7 is a flowchart illustrating an example method consistent with this disclosure.

FIG. 7 is a flowchart illustrating an example technique for programming IMD 16 for providing brain stimulation. IMD 16, via a combination of electrodes 24, 26, provides electrical stimulation to a patient's brain 28 at a specific frequency (210). The stimulation is provided to a stimulation site. In some examples, the stimulation site may be preselected based on known connectivity between the stimulation site and a target site. The specific frequency of stimulation may be selected based on a desired outcome of the stimulation, e.g., inhibition or excitation. The desired outcome may activity within brain 28 at a particular frequency. For example, if "normal" activity at a target site is at a particular frequency, the specific frequency of stimulation may be set at a frequency higher than the particular frequency such that the particular frequency is a sub-harmonic of the specific frequency. In some examples, the specific frequency may be a frequency known to provide a therapeutic effect to patient 12. IMD 16, via sensing module 66, senses bioelectrical brain activity in response to the electrical stimulation (212). The bioelectrical brain activity is sensed from a target site. In some examples the stimulation site and the target site are the same. In some examples, the stimulation site and the target site are in different regions of the brain. Processor 60 detects a biomarker in the sensed bioelectrical brain activity (214). In some examples, detection of the biomarker may be done by processor 80 of the external programmer 14. Detection may also be performed by a combination of processor 60 and processor 80. In some examples, the detected biomarker may be the presence of oscillation in the sensed bioelectrical response signal. In other examples, the detected biomarker may the presence of one or more peaks in the sensed bioelectrical response signal. In examples where the presence of oscillation in the sensed signal is the biomarker, the processor 60 may determine the length of time of oscillation (Tosc). Processor 80 compares Tosc to one or more predetermined thresholds. For example, Tosc may be compared to a minimum length of oscillation threshold T1 and a maximum length of oscillation threshold T2. In some examples, the oscillation may self terminate prior to the end of stimulation. In other examples, the oscillation may last until approximately the time stimulation is terminated.

Processor sets at least one electrical stimulation therapy parameter based on the detected biomarker (216). In some examples, the electrical stimulation parameter is set based on the comparison of Tosc to T1 and/or T2. T1 may be the minimum time of oscillation in order to obtain the desired therapeutic effect. T2 may be the time above which adverse effects are experienced. The length of a stimulation pulse may be adjusted for example based on the comparisons. In other examples, the amplitude of stimulation may be adjusted.

Figure 8:
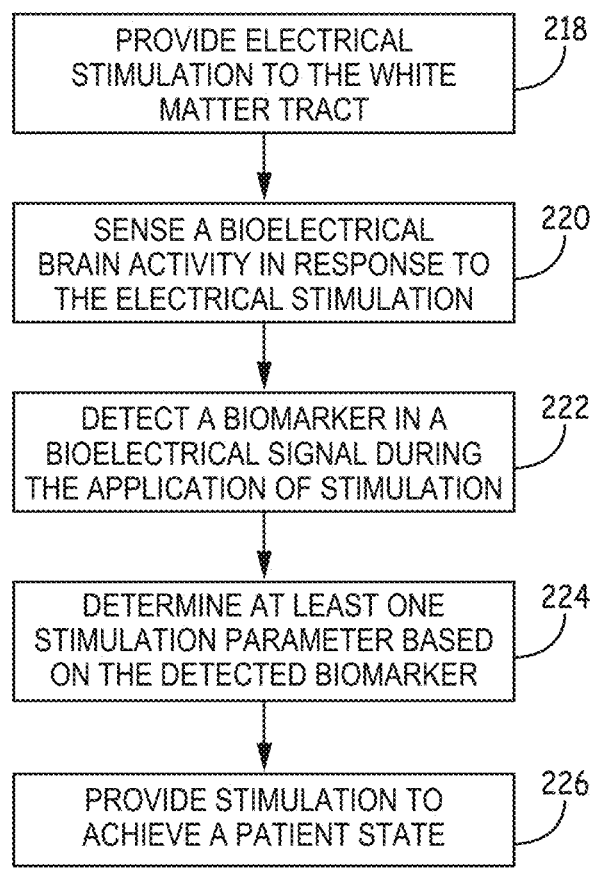
FIG. 8 is a flowchart illustrating an example method consistent with this disclosure.

FIG. 8 is an example technique, consistent with the present disclosure, directed to achieving or maintaining a patient state. IMD 16, via electrodes 24, 26, provides electrical stimulation to the white matter tract (218) of brain 28 of patient 12. The stimulation is delivered according to a set of stimulation parameters. The stimulation parameters may include, for example, a pulse width, a current amplitude, a voltage amplitude, a frequency, and an electrode combination for delivering the stimulation. IMD 16 provides stimulation to a stimulation site. The stimulation site may be selected based on a determination that the stimulation site has a neural connection to a target site for the effect of the stimulation. Sensing module 66 senses a bioelectrical brain signal in response to the electrical stimulation (220), during a stimulation pulse/ stimulation application. The bioelectrical brain signal may be sensed by the same electrodes that provide stimulation. The electrode combination providing stimulation may sense the bioelectrical brain signal using far-field sensing. In other examples, the signal may be sensed by a different electrode combination than the one providing stimulation. In some examples, the electrode combination sensing the bioelectrical brain activity may be adjacent to the target site.

Processor 60 detects a biomarker in the bioelectrical signal during the application of stimulation (222). The biomarker may be an oscillating portion of the signal, wherein the signal oscillates at one of a sub-harmonic frequency of the frequency of stimulation, or a physiologically driven frequency different from the frequency of stimulation. In other examples, the biomarker may be an excitatory response "chirp." A stimulation induced chirp includes an initial period of short acting inhibition followed by an excitatory response. The chirp may resemble an after-discharge in morphology. However, the chirp is different in that it is essentially confined to the period of stimulation. The chirp may be a biomarker of therapeutic effects or of adverse effects.

In some examples, the determination of whether the presence of a chirp indicates therapeutic effects or adverse effects may be patient-specific. For example, during programming of IMD 16, a patient may indicate whether the stimulation which induced the chirp is helpful or hurtful to a particular goal, such as increased cognition, memory recall, or mood. In some examples, whether or not the chirp is a biomarker of therapeutic effects or adverse effects may be determined based on the amplitude of the chirp. For example, a chirp with an amplitude above a certain predetermined threshold may be considered an indication of adverse effects on the patient. Similarly, an oscillation biomarker may also indicate therapeutic or adverse effects. In the case of the oscillation biomarker, the length of time of oscillation may be compared to one or more predetermined thresholds. If the length of time of oscillation is too short, it may indicate the stimulation is having no effect. If the length of time of oscillation is too long it may indicate an adverse effect.

Based on the analysis of the biomarker by processor 60 and/or processor 80, IMD 16 may determine at least one stimulation parameter based on the detected biomarker (224). For example, in the case the biomarker indicates an adverse effect, the intensity or period of stimulation may be decreased. In contrast, if the biomarker indicates effective therapy, then the stimulation parameters may be maintained. Stimulation generator 66, via electrodes 24, 26, provides stimulation to achieve a desired patient state (226). In some example, stimulation may be provided on an intermittent basis to provide excitatory drive to a neural circuit. For example, stimulation at a level which provide a chirp indicative of a therapeutic effect may be provided according to a therapy program. The therapy program may indicate how frequently stimulation should be provided in order to achieve or maintain a desired patient state. In other examples, the stimulation may be provided in response to patient input, for example. In still other examples, the stimulation may be provided as part of closed-loop, responsive, therapy. In other examples, the stimulation can alternatively or additionally be provided based on time of day and/or day of week. For instance, if it is known based on user input, time of day, day of week, etc., that an Alzheimer's patient is likely attempting to have a conversation, it may be desirable to provide excitatory stimulation to allow them to have better recall. On the other hand, if it is known based on time of day, day of week and/or user input that the patient is attempting to sleep, it may be desirable to turn off stimulation entirely to save battery power. In other cases, and for other therapies, inhibitory stimulation may be appropriate for some circumstances whereas excitatory stimulation may be better for others, as determined by any combination of the aforementioned factors.

Figure 9:
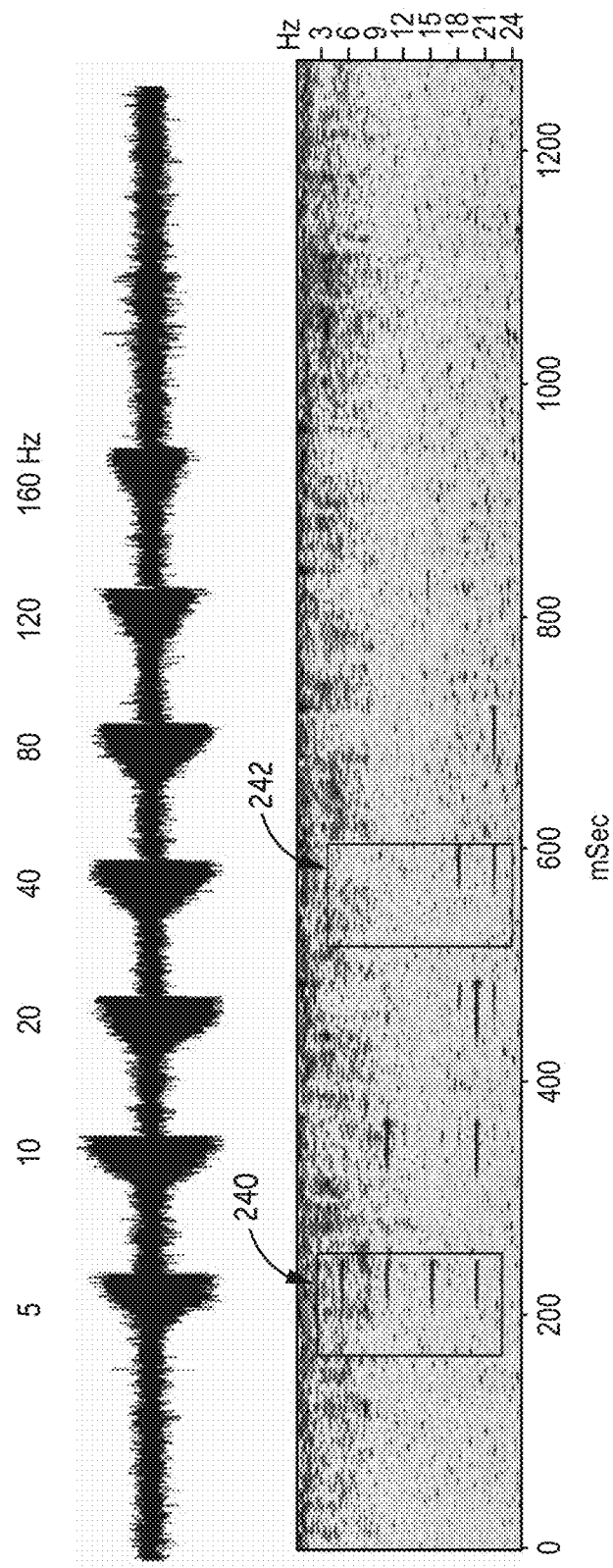
FIG. 9 is a graphical illustration of the response to stimulation at various frequencies.

FIG. 9 is a graph illustrating bioelectrical brain signals detected in response to stimulation applied to the white matter tract at various frequencies ranging from 5 Hz. To 160 Hz. The x-axis is time in msec, and the y-axis is in Hz. The application of stimulation is indicated in the top band. The different gradients of gray indicate activity detected at a particular frequency. The darker the band, the stronger the signal detected at the particular frequency. Stimulation was applied at a constant intensity, and for a constant period. As shown in box 240, stimulation provided at 5 Hz resulted in an excitatory response at a range of frequencies. Box 240 indicates the approximate period of stimulation. As shown in FIG. 9, the response to stimulation ends at approximately the same time the application of stimulation ends. Similarly, box 242 shows the approximate period of stimulation. At approximately 40 Hz, there is a short period of inhibition, followed by an excitatory response. As can be seen in FIG.

9, above a stimulation frequency of approximately 40 Hz, the excitatory effect dissipates as the stimulation frequency increases.

Figure 10:
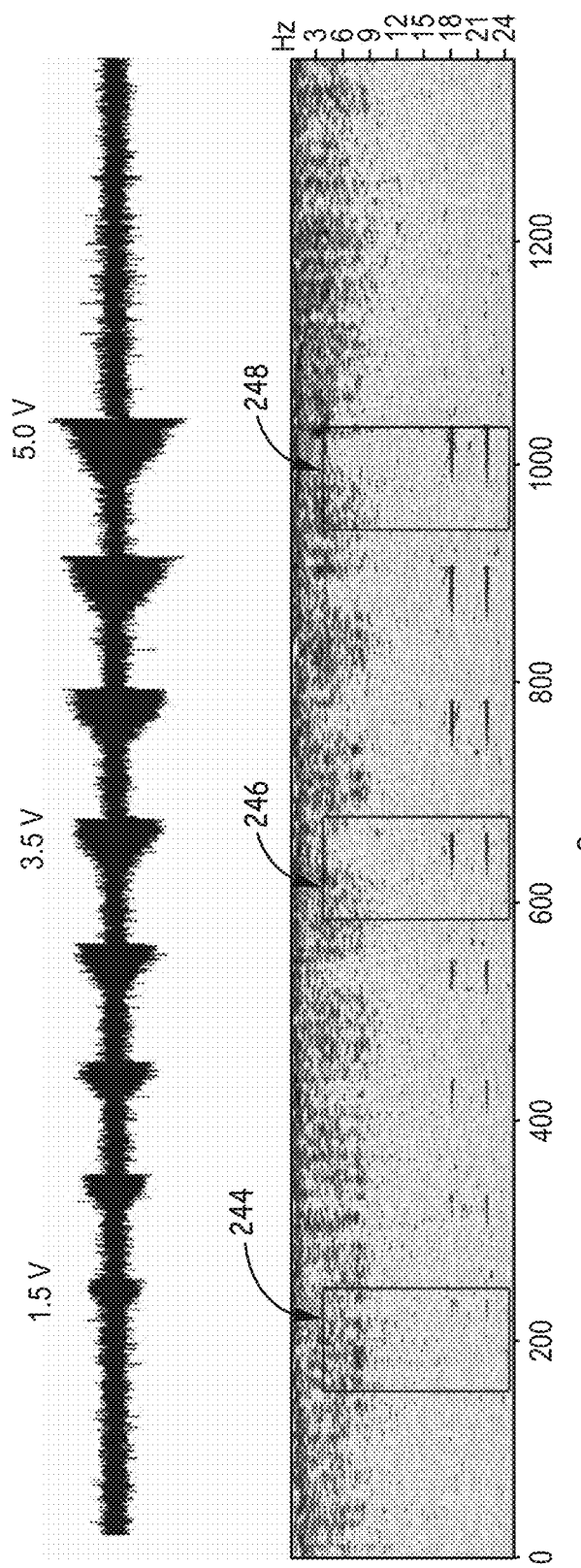
FIG. 10 is a graphical illustration of the response to stimulation at various amplitudes.

FIG. 10 is graph illustrating bioelectrical brain signals detected in response to stimulation applied to the white matter tract at various voltages ranging from 1.5 V to 5 V. The frequency of stimulation was held constant. The x-axis is time in msec, and the y-axis is in Hz. The application of stimulation is indicated in the top band. The different gradients of gray indicate activity detected at a particular frequency. The darker the band, the stronger the signal detected at the particular frequency. As in FIG. 10, boxes 244, 246, and 248 illustrate the period of stimulation. As is seen in FIG. 10, stimulation at low voltage results in little to no excitatory response; while as the voltage increases a period of inhibition followed by excitation is present. The response or "chirps" present in FIG. 10 end at approximately the same time the application of stimulation to the white matter tract ends.

Figure 11:
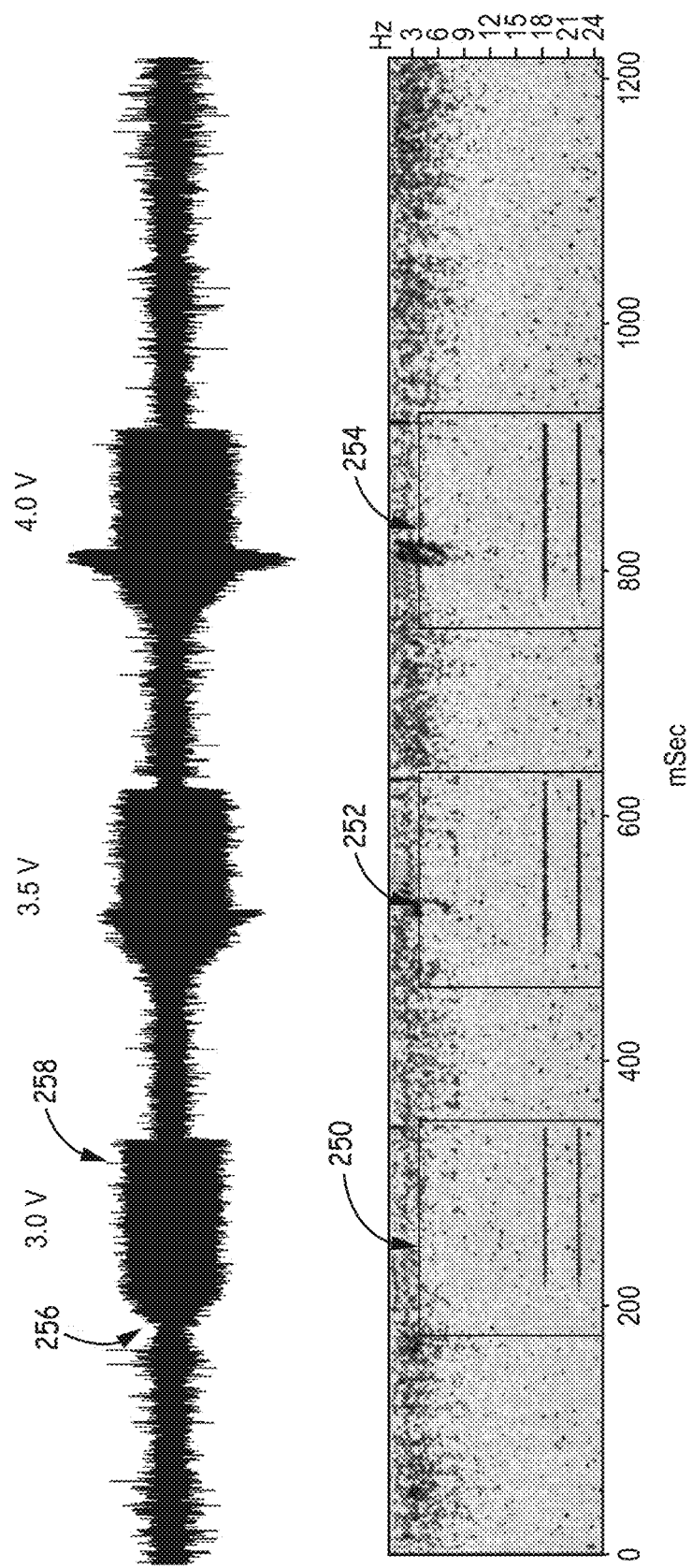
FIG. 11 is a graphical illustration of the response to stimulation at various amplitudes.

FIG. 11 shows a portion of FIG. 10 in greater detail. As with FIGS. 9 and 10, boxes 250, 252, and 254 indicate the period of stimulation. The x-axis is time in msec, and the y-axis is in Hz. The application of stimulation is indicated in the top band. The different gradients of gray indicate activity detected at a particular frequency. The darker the band, the stronger the signal detected at the particular frequency. As can be seen looking at the application of stimulation at 3 V, for example, the initial response 256 to stimulation is an inhibitory response. The initial response 256 is followed by an excitatory response 258.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples of the disclosure have been described. These and other examples are within the scope of the following claims.

What is claimed is:

1. A method comprising:
   delivering, via a plurality of electrodes implanted in a brain of a patient, electrical stimulation to a stimulation site of the brain of the patient, wherein the stimulation site comprises a neural connection to a target site of the brain of the patient, and wherein the stimulation site comprises a Fornix of the brain of the patient;
   sensing, via the plurality of electrodes and from the target site, bioelectrical brain activity comprising a bioelectrical response to the delivery of the electrical stimulation, the bioelectrical response overlapping in time with at least a portion of the delivery of the electrical stimulation;
   detecting, by processing circuitry, a biomarker in the bioelectrical response, the biomarker occurring during the delivery of the electrical stimulation;
   determining, by the processing circuitry, at least one parameter value of subsequent electrical stimulation based on the detected biomarker; and
   delivering, via the plurality of electrodes, the subsequent electrical stimulation according to the determined at least one parameter value to the stimulation site to achieve a patient state in the target site.

2. The method of claim 1, wherein the stimulation site and the target site are different.

3. The method of claim 1, wherein the stimulation site comprises a white matter tract of the brain of the patient.

4. The method of claim 1, wherein the biomarker comprises an oscillation in the bioelectrical response at a frequency that is a sub-harmonic frequency of a frequency of the electrical stimulation.

5. The method of claim 1, wherein the biomarker comprises an oscillation in the bioelectrical response at a frequency that is different than a frequency of the electrical stimulation.

6. The method of claim 1, wherein the biomarker comprises a chirp in the bioelectrical response, the chirp comprising a short acting inhibition in the bioelectrical response followed by an excitatory response in the bioelectrical response.

7. The method of claim 6, wherein the excitatory response in the bioelectrical response lasts until about an end of the electrical stimulation.

8. The method of claim 1,
   wherein determining the at least one parameter value of the subsequent electrical stimulation based on the detected biomarker comprises determining at least one parameter value of the subsequent electrical stimulation based on the detected biomarker to treat a condition of the patient, and
   wherein delivering the subsequent electrical stimulation according to the determined at least one parameter value to the stimulation site to achieve the patient state in the target site comprises delivering the subsequent electrical stimulation according to the determined at least one parameter value to the stimulation site to treat the condition of the patient.

9. The method of claim 1,
   wherein determining the at least one parameter value of the subsequent electrical stimulation based on the detected biomarker comprises determining at least one parameter value of the subsequent electrical stimulation based on the detected biomarker to mitigate one or more of symptoms of a disorder of the patient, and
   wherein delivering the subsequent electrical stimulation according to the determined at least one parameter value to the stimulation site to achieve the patient state in the target site comprises delivering the subsequent electrical stimulation according to the determined at least one parameter value to the stimulation site to mitigate the one or more of symptoms of the disorder of the patient.

10. The method of claim 1,
wherein determining the at least one parameter value of the subsequent electrical stimulation based on the detected biomarker comprises determining at least one parameter value of the subsequent electrical stimulation based on the detected biomarker to facilitate one of memory recall, cognitive function, or mood of the patient, and
wherein delivering the subsequent electrical stimulation according to the determined at least one parameter value to the stimulation site to achieve the patient state in the target site comprises delivering the subsequent electrical stimulation according to the determined at least one parameter value to the stimulation site to facilitate one of memory recall, cognitive function, or mood of the patient.

11. The method of claim 1, wherein prior to the step of delivering electrical stimulation, selecting, from a set of regions of the brain and based on the bioelectric brain activity, the Fornix as the stimulation site for delivering the electrical stimulation.

12. The method of claim 11, further comprising:
determining, based on the bioelectrical brain activity, a level of brain activity within the target site; and
selecting the Fornix as the stimulation site for delivering the electrical stimulation based on the level of brain activity within the target site.

13. The method of claim 1, wherein the target site comprises the hippocampus.

14. The method of claim 1, wherein the biomarker comprises an oscillation in the bioelectrical response, and wherein the method further comprises:
determining, based on the biomarker, a length of time of oscillation of the oscillation in the bioelectrical response;
comparing the length of time of oscillation to one or more threshold lengths of time of oscillation; and
determining the at least one parameter value of the subsequent electrical stimulation based on comparing the length of time of oscillation to the one or more threshold lengths of time of oscillation.

15. The method of claim 14, wherein the one or more threshold lengths of time of oscillation include:
a first threshold length of time of oscillation representing a minimum time of oscillation to achieve the patient state in the target site; and
a second threshold length of time of oscillation representing a time of oscillation above which adverse effects occur.

16. The method of claim 1, wherein the electrical stimulation delivered to the stimulation site elicits the bioelectrical response at the target site.

* * * * *